US008487006B2

(12) United States Patent
Huang et al.

(10) Patent No.: US 8,487,006 B2
(45) Date of Patent: Jul. 16, 2013

(54) METHOD OF ENHANCING TGF-β SIGNALLING

(75) Inventors: Jung San Huang, St. Louis, MO (US); Shuan Shian Huang, St. Louis, MO (US)

(73) Assignees: Auxagen, Inc., St. Louis, MO (US); Saint Louis University, St. Louis, MO (US)

( * ) Notice: Subject to any disclaimer, the term of this patent is extended or adjusted under 35 U.S.C. 154(b) by 709 days.

(21) Appl. No.: 12/560,136

(22) Filed: Sep. 15, 2009

(65) Prior Publication Data

US 2010/0075923 A1    Mar. 25, 2010

Related U.S. Application Data

(60) Provisional application No. 61/097,302, filed on Sep. 16, 2008.

(51) Int. Cl.
*A61K 31/166* (2006.01)
*C07C 245/04* (2006.01)
*C07C 39/21* (2006.01)

(52) U.S. Cl.
CPC .......... *A61K 31/166* (2013.01); *C07C 2101/16* (2013.01); *C07C 245/04* (2013.01)
USPC ............................................ 514/615; 560/56

(58) Field of Classification Search
None
See application file for complete search history.

(56) References Cited

U.S. PATENT DOCUMENTS

| 4,058,620 A * | 11/1977 | Westley ..................... 514/460 |
| 4,179,337 A | 12/1979 | Davis et al. |
| 4,423,037 A | 12/1983 | Rosenblatt et al. |
| 4,456,596 A | 6/1984 | Schafer |
| 4,666,907 A | 5/1987 | Fortin et al. |
| 4,959,314 A | 9/1990 | Mark et al. |
| 5,118,791 A | 6/1992 | Burnier et al. |
| 5,147,854 A | 9/1992 | Newman |
| 5,444,151 A | 8/1995 | Vassbotn et al. |
| 5,571,714 A | 11/1996 | Dasch et al. |
| 5,616,561 A | 4/1997 | Barcellos-Hoff |
| 5,624,938 A | 4/1997 | Pernis |
| 5,654,270 A | 8/1997 | Ruoslahti et al. |
| 5,693,607 A | 12/1997 | Segarini et al. |
| 5,824,297 A | 10/1998 | Iwata et al. |
| 5,981,606 A | 11/1999 | Martin |
| 5,981,621 A * | 11/1999 | Clark et al. .................. 523/118 |
| 6,068,845 A | 5/2000 | Aoki et al. |
| 6,075,005 A | 6/2000 | Lurie |
| 6,316,258 B1 | 11/2001 | Noble et al. |
| 6,337,320 B1 | 1/2002 | Hersh et al. |
| 6,500,920 B1 | 12/2002 | Haung |
| 6,649,588 B1 | 11/2003 | Tabibzadeh et al. |
| 6,806,358 B1 | 10/2004 | Bier et al. |
| 6,838,076 B2 | 1/2005 | Patton et al. |
| 6,906,026 B1 | 6/2005 | Noble et al. |
| 7,057,013 B1 | 6/2006 | Ezquerro Saenz et al. |
| 7,723,473 B2 | 5/2010 | Huang |
| 7,741,283 B2 | 6/2010 | Huang |
| 7,973,022 B2 * | 7/2011 | Murthy ........................... 514/58 |
| 8,110,655 B2 | 2/2012 | Huang et al. |
| 2003/0059447 A1 | 3/2003 | Lambers |
| 2004/0116407 A1 | 6/2004 | Borisy |
| 2004/0229791 A1 | 11/2004 | Huang |
| 2005/0250801 A1 * | 11/2005 | Shailubhai et al. ........... 514/278 |
| 2006/0153794 A1 | 7/2006 | Hibino et al. |
| 2006/0233708 A1 | 10/2006 | Huang |
| 2007/0053957 A1 | 3/2007 | Kennedy |
| 2007/0203097 A1 * | 8/2007 | Murthy ........................... 514/58 |
| 2008/0194690 A1 * | 8/2008 | Bastin et al. .................. 514/603 |
| 2008/0319010 A1 * | 12/2008 | Kastan et al. ................. 514/313 |
| 2009/0062247 A1 | 3/2009 | Huang et al. |
| 2011/0008248 A1 | 1/2011 | Huang |

FOREIGN PATENT DOCUMENTS

| EP | 0433225 B1 | 4/1999 |
| EP | 1132403 B1 | 5/2006 |
| GB | 2305123 A | 4/1997 |
| WO | 93/25225 A1 | 12/1993 |
| WO | 97/08196 A1 | 3/1997 |
| WO | WO98/04245 * | 2/1998 |
| WO | 0031135 A1 | 6/2000 |
| WO | 03093293 A2 | 11/2003 |
| WO | WO2004/080478 * | 9/2004 |
| WO | WO2005/049009 * | 6/2005 |
| WO | 2006138048 A2 | 12/2006 |
| WO | 2009029656 | 3/2009 |
| WO | WO2009/114700 * | 9/2009 |
| WO | 2010033507 | 3/2010 |

OTHER PUBLICATIONS

Mosley et al., "Neuroinflammation, Oxidative Stress and the Pathogenesis of Parkinson's Disease" Clin Neurosci Res (2006) vol. 6 No. 5 pp. 261-281.*
Negre-Aminou et al., "Inhibition of proliferation of human smooth muscle cells by various HMG-CoA reductase inhibitors; comparison with other human cell types" Biochimica et Biophysica Acta (1997) 1345 pp. 259-268.*
Kirchhausen et al., "Use of Dynasore, the Small Molecule Inhibitor of Dynamin, in the Regulation of Endocytosis" Methods in Enzymology (2008) vol. 438 pp. 77-93.*
Runyan, Constance E., et al., "TGFβ receptor-binding proteins: Complex interactions," Cellular Signalling, 18: 2077-2088 (2006).
Macia, Eric, et al., "Dynasore, a Cell-Permeable Inhibitor of Dynamin," Developmental Cell, 10: 839-850 (2006).

(Continued)

*Primary Examiner* — Eric S Olson

(57) ABSTRACT

The present invention is directed to a method of enhancing TGF-β signaling in a subject comprising administering to said subject a clathrin-dependent endocytosis inhibitor in an amount sufficient to enhance TGF-β signaling. In another aspect, the invention is directed to a method of treating a condition associated with decreased TGF-β signaling in a patient in need thereof comprising administering to said patient a clathrin-dependent endocytosis inhibitor in a therapeutically effective amount.

8 Claims, 13 Drawing Sheets

OTHER PUBLICATIONS

Chen, Chun-Lin, et al., "Cholesterol suppresses cellular TGFβ responsiveness: implications in atherogenesis," J. Cell Science, 120: 3509-3621 (2007).

Office action for Canadian Patent Application No. 2,484,994, dated Aug. 3, 2011, 3 pages.

Office action for Canadian Patent Application No. 2,699,454, dated May 13, 2011, 3 pages.

Office action for European Patent Application No. 03728390.0, dated Jan. 18, 2008, 9 pages.

Office action for U.S. Appl. No. 09/095,637, dated Aug. 30, 1999, 7 pages.

Office action for U.S. Appl. No. 09/095,637, dated May 23, 2000, 16 pages.

Office action for U.S. Appl. No. 09/095,637, dated Apr. 4, 2001, 11 pages.

Office action for U.S. Appl. No. 09/095,637, dated Aug. 21, 2001, 5 pages.

Office action for U.S. Appl. No. 09/095,637, dated Dec. 6, 2000, 6 pages.

Office action for U.S. Appl. No. 09/095,637, dated Nov. 28, 2001, 7 pages.

Office action for U.S. Appl. No. 10/135,946, dated Jan. 9, 2006, 12 pages.

Office action for U.S. Appl. No. 10/135,946, dated Jun. 21, 2005, 16 pages.

Office action for U.S. Appl. No. 10/748,703, dated Nov. 1, 2007, 6 pages.

Office action for U.S. Appl. No. 10/966,371, dated Dec. 15, 2008, 10 pages.

Office action for U.S. Appl. No. 10/966,371, dated Jan. 4, 2008, 8 pages.

Office action for U.S. Appl. No. 10/966,371, dated Oct. 15, 2008, 6 pages.

Office action for U.S. Appl. No. 11/432,125, dated Aug. 7, 2008, 15 pages.

Office action for U.S. Appl. No. 11/432,125, dated Jan. 13, 2009, 12 pages.

Office action for U.S. Appl. No. 11/432,125, dated Jun. 24, 2009, 10 pages.

Office action for U.S. Appl. No. 11/939,126, dated Jan. 7, 2011, 5 pages.

Office action for U.S. Appl. No. 11/939,126, dated May 14, 2010, 7 pages.

Office action for U.S. Appl. No. 12/199,459, dated Aug. 19, 2010, 10 pages.

Office action for U.S. Appl. No. 12/199,459, dated Jan. 26, 2011, 16 pages.

O'Grady et al., Purification of a New Type High Molecular Weight Receptor (Type V Receptor) of Transforming Growth Factor β (TGF-β) from Bovine Liver, J. Biol. Chem. 266:8583-8589 (1991).

O'Kane, et. al., Transforming Growth Factors Bs and Wound Healing, Elsevier Science Ltd., 1997, pp. 63-78.

Postlethwaite et al., Identification of a chemotactic epitope in human transforming growth factor-beta 1 spanning amino acid residues 368-374., J Cell Physiol. Sep. 1995; 164(3):587-92.

Qian et al. Identification of a structural domain that distinguishes the actions of the type 1 and 2 isoforms of transforming growth factor beta on endothelial cells. Proc Natl Acad Sci., Jul. 15, 1992;89(14):6290-4.

Qian et al., "Binding affinity of transforming growth factor-beta for its type 11 receptor is determined by the C-terminal region of the molecule." J Biol Chem. Nov. 29, 1996; 271(48):30656-62.

Qian et al., "Characterization of mutated transforming growth factor beta- s which possess unique biological properties." Biochemistry. Oct. 11, 1994; 33(40): 12298-304.

Qian et al., "Distinct functional domains of TGF-beta bind receptors on endothelial cells." Growth Factors. 1999; 17 (1):63-73.

Ricort et al., "Insulin-like Growth Factor-binding Protein-3 Activates a Phosphotyrosine Phosphatase," J. Biol. Chem., May 31, 2002, vol. 277, No. 22, pp. 19448-19454.

Rocha et al., "Insulin-like Growth Factor Binding Protein-3 and Insulin Receptor Substrate-1 in Breast Cancer: Correlation with Clinical Parameters and Disease-free Survival," Clin. Can. Res., Jan. 1997, vol. 3, pp. 103-109.

Rudinger, J. "Characteristics of the amino acids as components of a peptide hormone sequence," Peptide Hormones, Jun. 1976, University Park Press.

Schlunegger et al., "Refined crystal structure of human transforming growth factor beta 2 at 1.95 A resolution." J Mol Biol. May 20, 1993; 231(2):445-58.

Schlunegger et al., An unusual feature revealed by the crystal structure at 2.2A resolution of human transforming growth factor-β2, Nature, 358:430-434 (1992).

Shah, et al., Neutralising Antibody to TGF-B1,2 Reduces Cutaneous Scarring in Adult Rodents, Journal of Cell Science, 1994, pp. 1137-1157.

Shah, et. al., "Neutralisation of TGF-β, and TRG-β2 or Exogenous Addition of TGF-β3 to Cutaneous Rat Wounds Reduces Scarring," Journal of Cell Science, Mar. 1995, 108 (Pt 3):985-1002.

Supplementary European Search Report for European Patent Application No. 03728390.0, dated Oct. 4, 2007, 3 pages.

Tanaka et al., "Insulin Receptor Substrate 1 Overexpression in Human Hepatocellular Carcinoma Cells Prevents Transforming Growth Factor β1-induced Apoptosis," Cancer Res., Aug. 1, 1996, 56(15), pp. 3391-3394.

Valencia et al., "7-dehydrocholesterol Enhances Ultraviolet A-Induced Oxidative Stress in Keratinocytes: Roles in Nadph Oxidative, Mitochondria and Lipid Rafts," Free Radic. Biol. Med., 2006, vol. 41, No. 11, pp. 1704-1718.

Van Scott et al., "Detection of Radiation Effects on Hair Roots of the Human Scalp," Journal of Investigative Dermatology, (1957), 29(3), pp. 205-212.

Written Opinion for PCT Application No. PCT/US09/56994, mailed Dec. 9, 2009, 4 pages.

Written Opinion for PCT Application No. PCT/US2008/74446, mailed Nov. 26, 2008, 5 pages.

Xia, et al., "Effects of Keratinocyte Growth Factor-2 (KGF-2) on Wound Healing in an Ischaemia-Impaired Rabbit Ear Model and on Scar Formation," Journal of Pathology, 1999, pp. 431-438.

Zambruno, et al., "Transforming Growth Factor-β1 Modulates β1 and β5 Integrin Receptors and Induces the de novo Expression of the αvβ6 Heterodimer in Normal Human Keratinocytes," Implications for Wound Healing, May 1995, pp. 853-865, The Rockefeller University Press.

Web, et al., Transforming Growth Factor β Isoform 2-specific High Affinity Binding to Native α2-Macroglobulin, J. Biological Chem., 1994, pp. 30402-30406, vol. 269, No. 48.

Office action for Canadian Application No. 2,484,994, dated Jun. 7, 2010, 4 pages.

Minutes of the Oral Proceedings dated Oct. 29, 2009 for related European Patent Application No. 03728390.0, 25 pages.

Statements of the Grounds for Appeal dated Mar. 8, 2010 for related European Patent Application No. 03728390.0, 36 pages.

Summons to Oral Proceedings dated Jul. 17, 2009 for related European Patent Application No. 03728390.0, 9 pages.

Amendt, et al., "Resistance of Keratinocytes to TGFB-Mediated Growth Restriction and Apoptosis Induction Accelerates Re-epithelialization in Skin Wounds," Journal of Cell Science, 2002, pp. 2189-2198.

Ashcroft, et al., "Mice Lacking Smad3 Show Accelerated Wound Healing and an Impaired Local Inflammatory Response," Nature Cell Biology, Sep. 1999, pp. 260-266.

Bowie et al., "Deciphering the message in protein sequences: tolerance to amino acid substitutions." Science, Mar. 16, 1990, vol. 247 (4948) 1306-10.

Burmester et al., "Characterization of distinct functional domains of transforming growth factor beta." Proc Natl Acad Sci USA. Sep. 15, 1993; 90(18):8628-32.

Burmester et al., "Mutational analysis of a transforming growth factor-beta receptor binding site." Growth Factors. 1998, 15(3):23142.

Chan, et al., "Accelerated Skin Wound Healing in Plasminogen Activator Inhibitor-1-Deficient Mice," American Journal of Pathology, Nov. 2001, pp. 1681-1688.

Chen et al: "Inhibitors of clathrin-dependent endocytosis enhance TGF signaling and responses", Journal of Cell Science, vol. 122, No. 11,May 20, 2009, pp. 1863-1871.

Chow et al., "Reduction in Rate of Growth of Hair in Mice as an Indicator of Exposure to Chronic Low Dosage Ionizing Radiation," Nature, Aug. 22, 1964, 203, No. 4947, pp. 847-848.

Daopin et al., "Crystal structure of transforming growth factor-beta 2: an unusual fold for the superfamily." Science. Jul. 17, 1992; 257(5068):369-73.

Darlak et al., "Assessment of biological activity of synthetic fragments of transforming growth factor-alpha." J Cell Biochem. Apr. 1988; 36(4):341-52.

Das, "Free radicals, cytokines and nitric oxide in cardiac failure and myocardial infarction," Molecular and Cellular Biochemistry, 2000, 215: 145-152.

Demetriou et al., "Fetuin/α2-HS Glycoprotein Is a Transforming Growth Factor-β Type II Receptor Mimic and Cytokine Antagonist," J. Biol. Chem., May 31, 1996, vol. 271, No. 22, pp. 12755-12761.

Derynck et al., Human transforming growth factor-f complementary DNA sequence and expression in normal and transformed cells, Nature 316:701-705 (1985).

Di Guglielmo et al., "Distinct endocytic pathways regulate TGF-[beta] receptor signalling and turnover", Nature Cell Biology, vol. 5, No. 5, Apr. 28, 2003, pp. 410-421.

Extended European Search Report for European Patent Application No. 08798785.5, dated Jul. 27, 2010, 7 pages.

Extended European Search Report for European Patent Application No. 09815064.2, dated Jan. 19, 2012, 8 pages.

Grainger et al., "Transforming Growth Factor Beta is Sequestered into an Inactive Pool by Lipoproteins," J. Lipid Res. 1997 vol. 38, No. 11, pp. 2344-2352.

Hinck et al., Transforming Growth Factor 31: Three-Dimensional Structure in Solution and Comparison with the X-ray Structure of Transforming Growth Factor β 2, Biochemistry 35:8517-8534 (1996).

Huang et al., A Pentacosapeptide (CKS-25) Homologous to Retroviral Envelope Proteins Possesses a Transforming Growth Factor-f Activity, J. Biol. Chem. 273:4815-4818 (1998).

Huang et al., Activated Thyroglobulin Possesses a Transforming Growth Factor-βActivity, J. Biol. Chem. 273:26036-26041 (1998).

Huang et al., Amyloid β-Peptide Possesses a Transforming Growth Factorβ Activity, J. Biol. Chem. 273-27640-17644 (1998).

Huang, et al., "An Active Site of Transforming Growth Factor B, for Growth Inhibition and Stimulation," The Journal of Biological Chemistry, Sep. 24, 1999, p. 27754-27758.

Huang, et al., "Synthetic TGF-B Antagonist Accelerates Wound Healing and Reduces Scarring," FASEB Journal, pp. 1-2, Aug. 2002.

Huang, et al., "Synthetic TGF-B Antagonistic Accelerates Wound Healing and Reduces Scarring," FASEB Journal, Aug. 2002; 16(10):1269-70. Epub Jun. 21, 2002.

Huang, et al., "Transforming Growth Factor B Peptide Antagonists and Their Conversion to Partial Agonists," The Journal of Biological Chemistry, Oct. 24, 1997, pp. 27155-27159.

Huynh et al., "A Possible Role for Insulin-like Growth Factor-binding Protein-3 Autocrine/Paracrine Loops in Controlling Hepatocellular Carcinoma Cell Proliferation," Cell Growth & Diff., Mar. 2002, vol. 13, pp. 115-122.

Inoue, M.D. et al., TGF-beta-2 is specifically expressed in human dermal papilla cells and modulates hair folliculogenesis, Journal of Cellular and Molecular Medicine, dated Oct. 16, 2008 (29 pages).

International Search Report for PCT Application No. PCT/US09/56994, mailed Dec. 9, 2009, 2 pages.

International Search Report for PCT Application No. PCT/US2003/11437, mailed Feb. 10, 2005, 1 page.

International Search Report for PCT Application No. PCT/US2008/74446, mailed Nov. 26, 2008, 2 pages.

Juengst, "What Next for Human Gene Therapy?," BMJ, Jun. 28, 2003, 326(7404), pp. 1410-1411.

Kingsley DM. The TGF-beta superfamily: new members, new receptors, and new genetic tests of function in different organisms. Genes Dev. Jan. 1994;8(2):133-46.

Laiho et al., Concomitant Loss of Transforming Growth Factor (TGF)- β Receptor Types I and II in TGF- β -resistant Cell Mutants Implicates Both Receptor Types in Signal Transduction, J. Biol. Chem. 265:18518-18524 (1990).

Leal et al., "The Type V Transforming Growth Factor β Receptor is The Putative Insulin-like Growth Factor-binding Protein 3 Receptor," Aug. 15, 1997, vol. 272, No. 33, pp. 20572-20576.

Limbird, L.L. "Identification of Receptors Using Direct Radioligand Binding Techniques," Chapter 3 in Cell Surface Receptors: A Short Course on Theory and Methods, 2nd ed., Kluwer Academic Publishers, Massachusetts, 1996, pp. 61-65.

Ling, T-Y, et al., "Fatty acids modulate transforming growth factor-beta activity and plasma clearance," The FASEB Journal, Jun. 3, 2003.

Liu et al., "Function of Type V Transforming Growth Factor β Receptor in Transforming Growth Factor β-induced Growth Inhibition of Mink Lung Epithelial Cells," J. Biol. Chem., Jul. 25, 1997, vol. 272, No. 30, pp. 18891-18895.

Liu, et al., "Identification of the High Affinity Binding Site in Transforming Growth Factor-B Involved in Complex Formation with a2-Macroglobulin," The Journal of Biological Chemistry, Dec. 7, 2001, pp. 46212-46218.

Madisen et al., Transforming Growth Factor-β2: eDNA Cloning and Sequence Analysis, DNA7:1-8 (1988).

McDonald et al. A structural superfamily of growth factors containing a cystine knot motif. Cell. May 1993, 7;73 (3):421-4.

Miller et al. GenBank Database Accession No. M32745. National Center for Biotechnology Information, Bethesda, MD. Apr. 27, 1993.

Mittl et al. The crystal structure of TGF-beta 3 and comparison to TGF-beta 2: implications for receptor binding. Protein Science, (Jul. 1996) 5 (7) 1261-71.

Mousavi et al., "Clathrin-dependent endocytosis", Biochemical Journal, vol. 377, No. I, Jan. 1, 2004, pp. 1-16.

Mustoe, et al., "Growth Factor-induced Acceleration of Tissue Repair Through Direct and Inductive Activities in a Rabbit Dermal Ulcer Model," Feb. 1991, pp. 694-703.

Ngo et al., The Protein Folding Problem and Tertiary Structure Prediction, Merz and Le Grand (Eds), Aug. 1994, Springer Verlag, pp. 433 and 492-495.

Notice of Allowance for Canadian Patent Application No. 2,699,454, dated Nov. 28, 2011, 1 page.

Notice of Allowance for U.S. Appl. No. 09/095,637, dated Jun. 10, 2002, 4 pages.

Notice of Allowance for U.S. Appl. No. 10/966,371, dated Jul. 14, 2009, 6 pages.

Notice of Allowance for U.S. Appl. No. 11/432,125, dated Dec. 22, 2009, 5 pages.

Notice of Allowance for U.S. Appl. No. 11/939,126, dated Sep. 23, 2011, 8 pages.

Written Submission dated Aug. 27, 2009 for related European Patent Application No. 03728390.0, 33 pages.

Office Action dated May 29, 2012 for related Chinese Patent Application No. 200980136369.2; 5 pages.

* cited by examiner

METHOD OF ENHANCING TGF-β SIGNALLING

RELATED APPLICATION

This application claims the benefit of U.S. Provisional Application No. 61/097,302, filed on Sep. 16, 2008. The entire teachings of the above application are incorporated herein by reference.

GOVERNMENT SUPPORT

This invention was made with government support under grant numbers AR052578 and HL087463 awarded by National Institutes of Health. The government has the rights in the invention.

BACKGROUND OF THE INVENTION

Transforming growth factor (TGF-β) is a family of pleiotrophic cytokines that inhibits the growth of most cell types (including epithelial cells, endothelial cells and lymphocytes). In mammals, the TGF-β family includes TGF-β1, -β2 and -β3. TGF-β is the most potent known stimulator for extracellular matrix synthesis and deposition and plays an important role in wound healing and tissue fibrosis. It has anti-inflammatory and pro-inflammatory activities, depending on the tissue studied.

Among its anti-inflammatory activities, TGF-β suppresses the activity of T cells, B cells, macrophages and NK cells and inhibits the expression of several proinflammatory genes (Piccirillo et al., (1998) J. Immunol. 161, 3950-3956; Prud'homme and Piccirillo, (2000) J. Autoimmun. 14, 23-42; Li, M. et al., (2006) Biochem. Biophys. Res. Commun. 344, 701-707). Because of its growth regulatory, anti-inflammatory and immunomodulatory activities, TGF-β has been identified as a target in the treatment of several diseases. For example, TGF-β somatic gene therapy has been shown to prevent autoimmune disease in nonobese diabetic mice (Piccirillo et al., (1998) J. Immunol. 161: 3950-3956). Injection of TGF-β1 has also been demonstrated to protect mice against collagen-induced arthritis (Kuruvilla et al., (1991) PNAS 88, 2918-2921) relapsing experimental allergic encephalomyelitis (Johns et al., (1991) J. Immunol. 147, 1792-1796), models for rheumatoid arthritis and multiple sclerosis, respectively and allograft rejections (Wallick et al., (1990) J. Exp. Med. 172, 1777-1784). TGF-β has additionally been shown to play a role in atherosclerosis in the cardiovascular system (Grainger D. J. (2004), Arterioscler. Thromb. Vasc. Biol., 24, 399-304; Metcalfe and Grainger (1995), Biochem. Soc. Trans. 23, 403-406). For example, it has been shown that one mechanism by which elevated cholesterol contributes to atherosclerosis is by decreasing the responsiveness of vascular cells to TGF-β (Chen et al., (2007) J. Cell Sci. 120, 3509-3521). TGF-β additionally plays a complex role in carcinogenesis. The cytokine is believed to possess tumor suppressor activity early in carcinogenesis but in later stages, tumor suppressor activity is lost and TGF-β acts as a growth-promoting agent (Derynck et al., (2001) J. Nat. Genet 29, 117-129); Piek and Roberts (2001) Adv. Cancer Res. 83, 1-54; Stover et al., (2007), J. Cell Biochem. 101, 851-861). Other conditions or diseases associated with decreased TGF-beta signaling include Alzheimers disease (Tesseur et al., (2006) J Clin Invest. 116, 3060-3069; Das et al., (2006) J. Clin. Invest. 116: 2855-2857), systemic lupus erythematosus (Ohtsuka et al., (1998) J. Immunol., 160: 2539-2545), chronic wounds (Kim et al., (2003). J. Cell. Phys., 195(3): 331-6), chronic obstructive pulmonary disease (Baraldo et al., (2005) Thorax; 60: 998-1002), inflammatory bowel disease (Fiocchi et al., (2001), J. Clin. Invest. 108(4): 523-526), Guillain-Barre syndrome (Creange et al., (1998), J Neurol Neurosurg Psychiatry 64: 162-165), and Colorectal cancer (Markowitz et al., Science 268, 1336 (1995), Valle et al., (2008) Science: 321, 1361).

Because TGF-β has utility in the treatment of several diseases and conditions, it would be useful to identify agents that enhance TGF-β signaling or increase cells' responsiveness to TGF-β.

SUMMARY OF THE INVENTION

The present invention is based on the surprising discovery that clathrin-dependent endocytosis inhibitors enhance TGF-β signaling. As shown in Example 1, the clathrin-dependent endocytosis inhibitors enhance TGF-β-induced signaling (TGF-β-stimulated Smad2 phosphorylation and nuclear localization).

The present invention is directed to a method of enhancing TGF-β signaling in a subject comprising administering to said subject a clathrin-dependent endocytosis inhibitor in an amount sufficient to enhance TGF-β signaling.

In another aspect, the invention is directed to a method of treating a condition associated with decreased TGF-β signaling in a patient in need thereof comprising administering to said patient a clathrin-dependent endocytosis inhibitor in a therapeutically effective amount.

In an additional aspect, the invention is a method of inhibiting carcinogenesis in a patient in need thereof comprising administering to said patient a clathrin-dependent endocytosis inhibitor in a therapeutically effective amount.

In a further embodiment, the invention is a pharmaceutical composition comprising a therapeutically effective amount of a clathrin-dependent endocytosis inhibitor and a therapeutically effective amount of an HMG-CoA reductase inhibitor.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
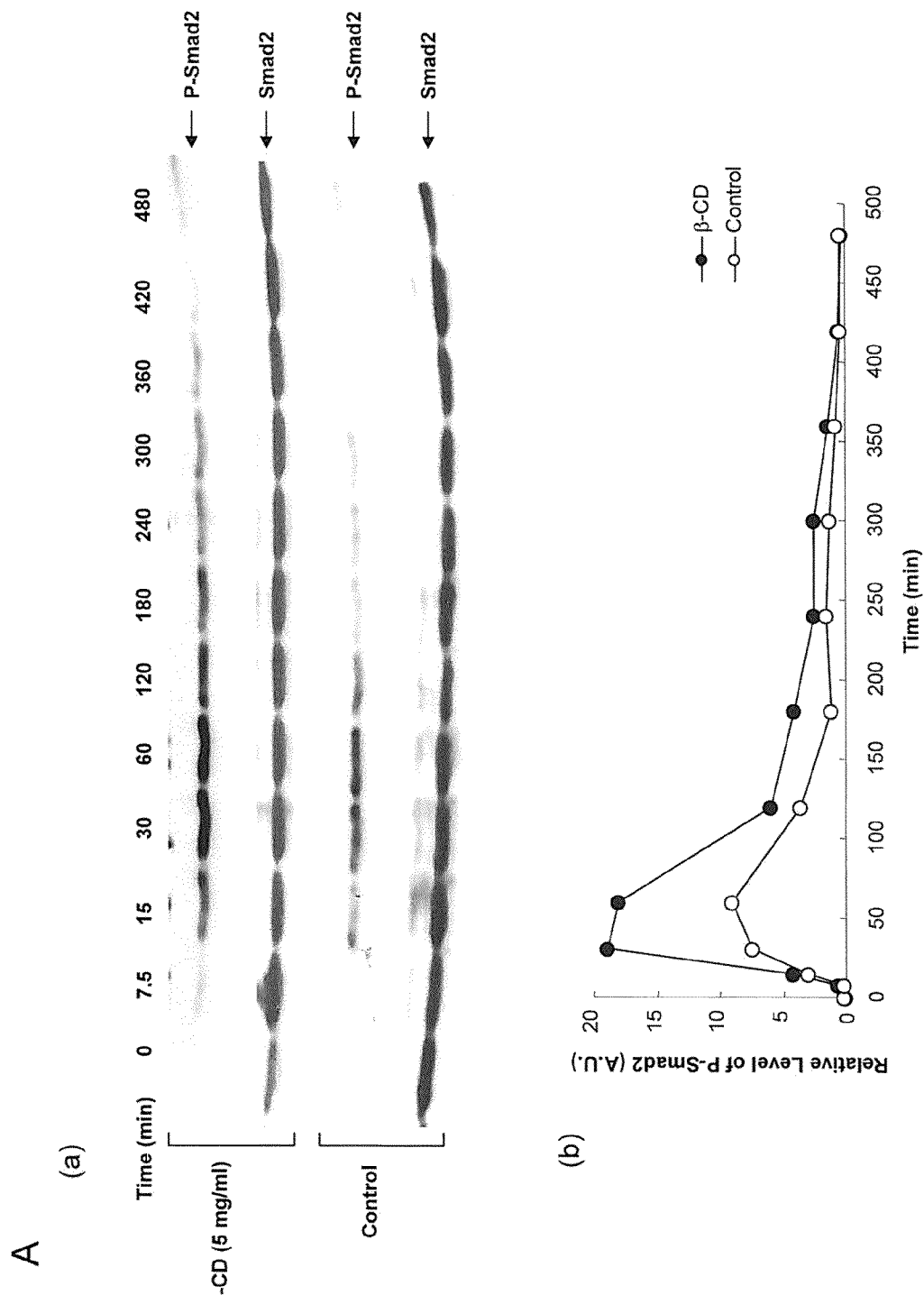
FIG. 1 shows enhancement of TGF-β-stimulated Smad2 phosphorylation and nuclear localization by clathrin-dependent endocytosis inhibitors in Mv1Lu cells. (A-I, K) Cells were pretreated with 10 mg/ml β-CD (A, K), 20 LM MDC (B), 40 μM monensin (C), 20 μM TFP (D) and 0.45 M sucrose (K) or several concentrations (as indicated) of β-CD (E), TFP (F), monensin (G), chloroquine (H), dynasore (I), at 37° C. for 1 h. The cells were then stimulated with vehicle only or 100 μM TGF-β$_1$ (A to I) or several concentrations (as indicated) of TGF-β$_1$ (K). After several time periods, as indicated, at 37° C., cell lysates were analysed by 7.5% SDS PAGE followed by Western blot analysis using antibodies to P-Smad2 and Smad2 and chemiluminescence development (a or top) and quantitation by densitometry (b or bottom). The relative level of P-Smad2 was expressed as arbitrary units (A.U.) (A, B, C, D, K) (b). The relative level of P-Smad2 in cells treated with TGF-β alone was taken as 100% of control (E to I, bottom). The data shown is representative of 3 independent experiments. (J) Cells were pretreated with 10 mg/ml β-CD (c,d) at 37° C. for 1 h. The cells were then stimulated with vehicle only (a) or with 100 pM TGF-β (b,d). After 30 min at 37° C. the cells were fixed and subjected to indirect immunofluorescent staining using antibody to P-Smad2. The magnification is 200×. The data shown is representative of 3 independent experiments.
Figures 1B, 1C, 1D:
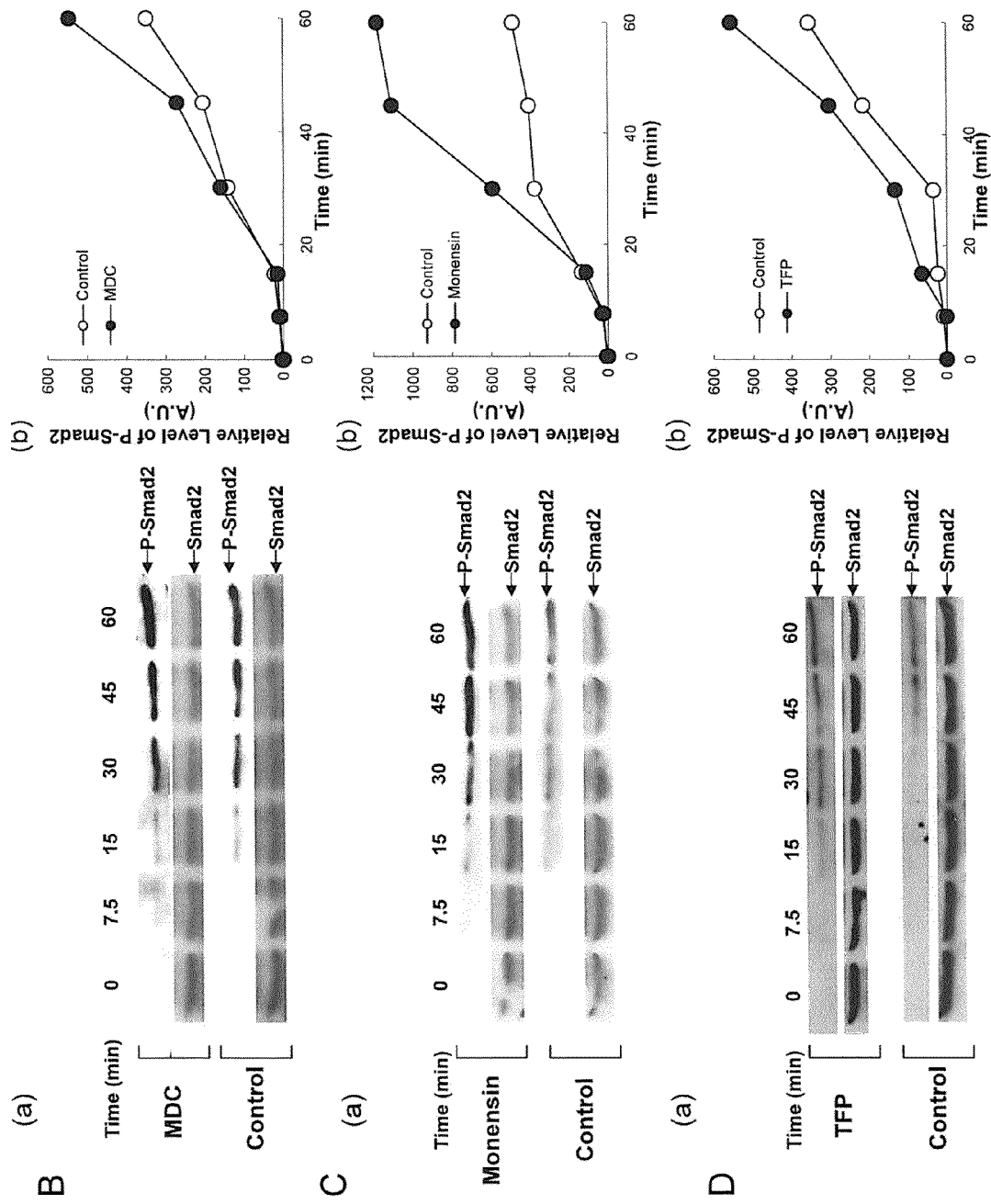
Figures 1E, 1F, 1G, 1H:
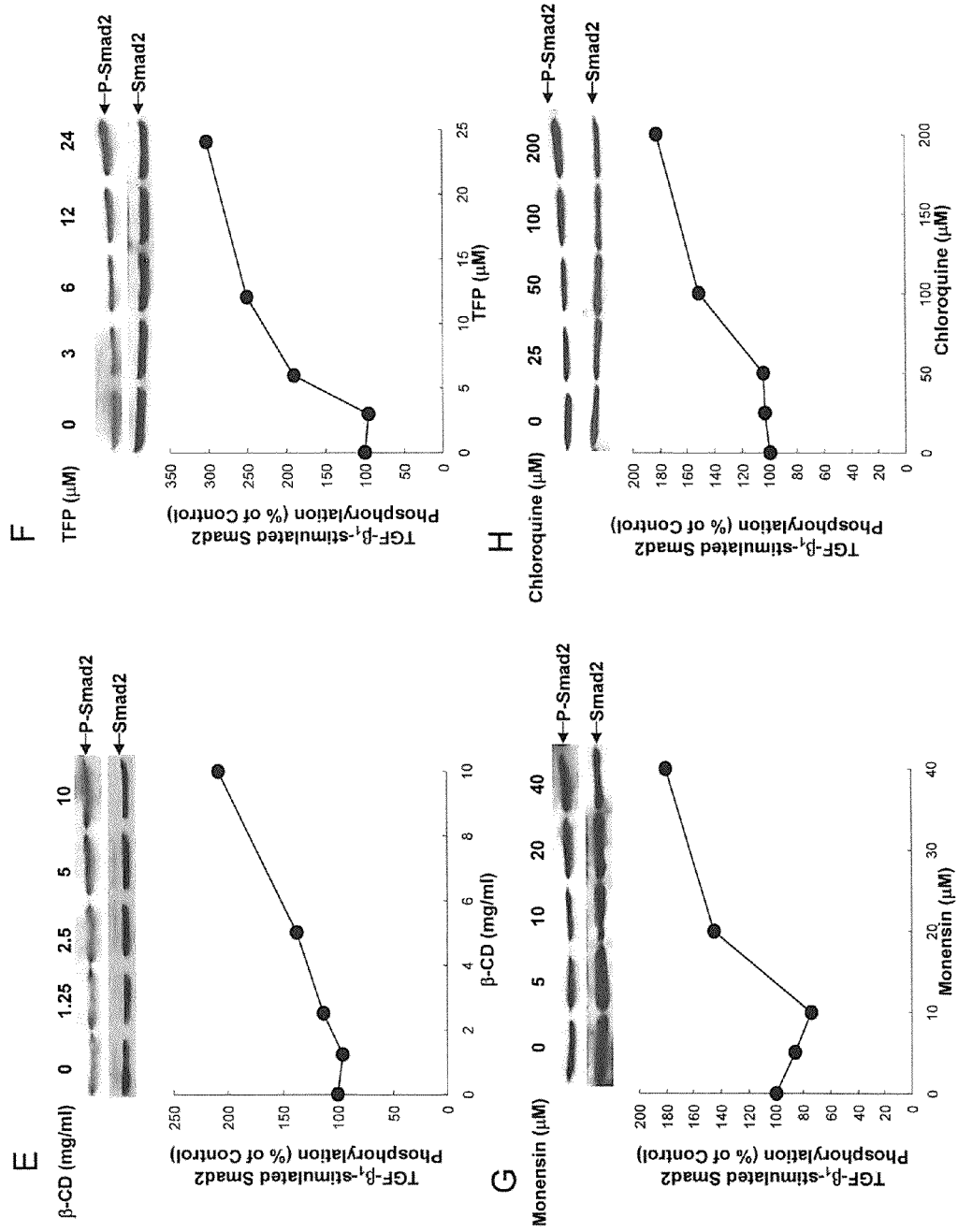
Figure 1I:
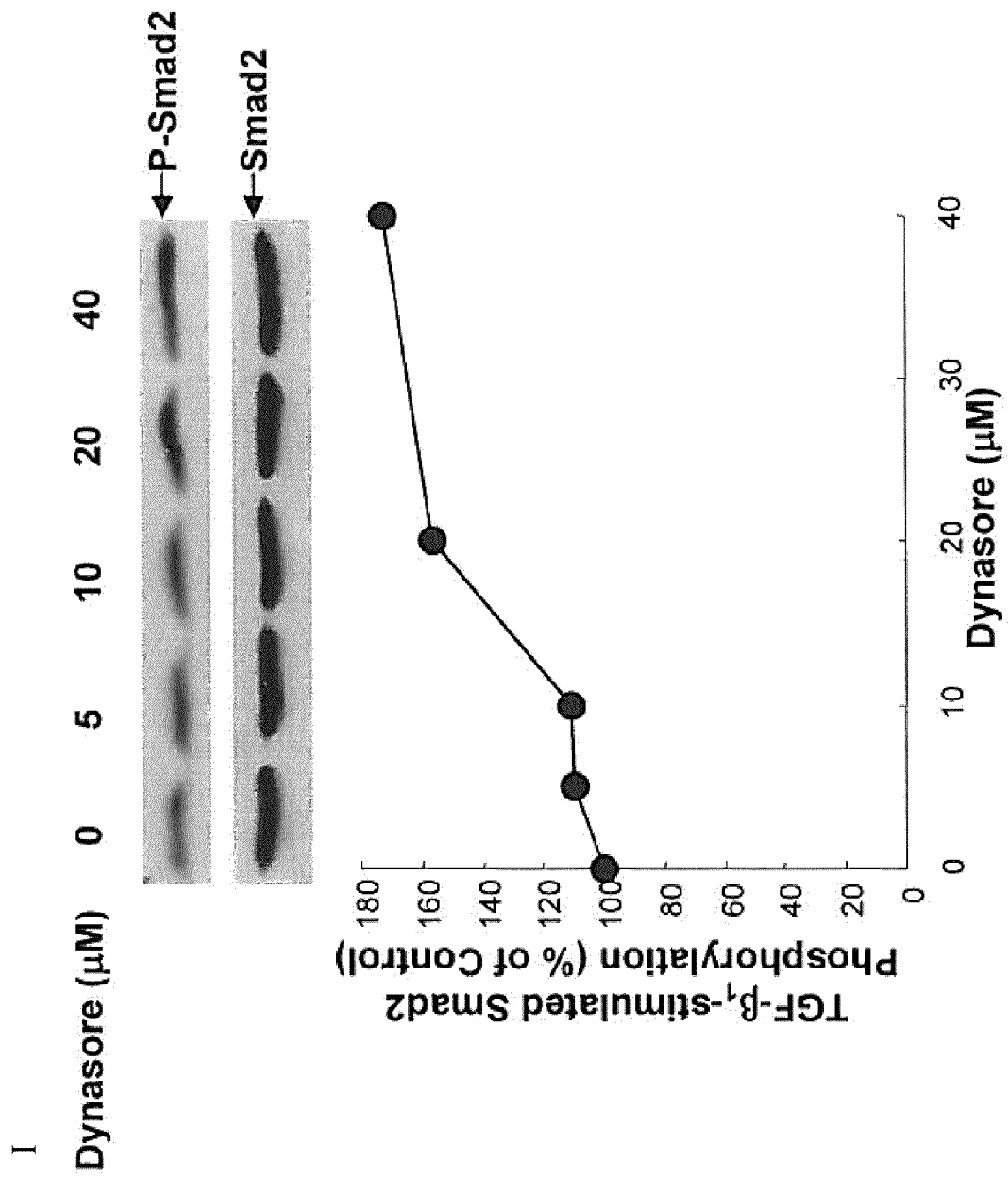

A description of preferred embodiments of the invention follows.

As used herein, "a" or "an" is meant to encompass one or more unless otherwise specified.

The present invention is directed to methods of enhancing TGF-β signaling or increasing TGF-β responsiveness comprising administering a clathrin-dependent endocytosis inhibitor. The invention is also directed to the treatment of diseases or conditions which can be ameliorated by enhancement of TGF-β signaling or increasing TGF-β responsiveness.

As used herein, the term "TGF-β" encompasses TGF-$β_1$, TGF-$β_2$, TGF-$β_3$ and TGF-β mutants, (e.g. TGF-β proteins exhibiting similar-biological activities and differing from the native TGF-β proteins by simple or multiple mutations, e.g. replacement, addition or omission of one or more amino acids).

TGF-β signaling is enhanced when the level of TGF-β in the plasma is increased or when the responsiveness of a cell to TGF-β signaling is increased. The level of TGF-β in the plasma can vary under different conditions. For example, the level of TGF-β in the plasma can be increased when the expression of a TGF-β gene in tissue cells is increased or when the turnover of TGF-β is inhibited. A cell's responsiveness to TGF-β can be increased by enhancing TGF-β signaling. For example, chatherin-dependent endocytosis inhibitors enhance cellular responsiveness to TGF-β by enhancing TGF-β-stimulated Smad2 phosphorylation. Eukaryotic cells utilize both clathrin-dependent and clathrin-independent endocytic pathways. Clathrin-dependent endocytosis is characterized by three stages: formation of the coated pit, invagination of the coated pits and pinching off of the coated vesicles (Mousavi et al., 2004). As used herein, a "clathrin-dependent endocytosis inhibitor" is an agent that inhibits clathrin-dependent endocytosis by any mechanism. Exemplary clathrin-dependent endocytosis inhibitors that can be used according to the invention are methyl-β-cyclodextrin (β-CD), hydrophobic amines (such as phenothiazines, monodansylcadaverine and chloroquine), monensin, hyperosmotic sucrose and dynasore. Phenothiazines include, but are not limited to, chlorpromazine, fluphenazine, mesoridazine, perphenazine, prochlorperazine, promazine, thioridazine, trifluoperazine and triflupromazine. β-CD inhibits clathrin-dependent endocytosis by selectively removing cholesterol from the plasma membrane. Hydrophobic amines inhibit clathrin-dependent endocytosis by affecting the function of clathrin and clathrin-coated vesicles. Monensin inhibits clathrin-dependent endocytosis by dissipating a proton gradient. Hyperosmotic sucrose inhibits clathrin-dependent endocytosis by preventing clathrin and adaptors from interacting. Dynasore inhibits dynamin GTPase which facilitates the formation of coated pits.

In one embodiment, the clathrin-dependent endocytosis inhibitor inhibits the pinching of the vesicle from the plasma membrane. In another embodiment, the clathrin-dependent endocytosis inhibitor is capable of stimulating PAI-1 expression (PAI-1 is a gene responsive to TGF-B stimulation). In an additional embodiment, the clathrin-dependent endocytosis inhibitor is dynasore, which itself exhibits TGF-β activity and is a TGF-β mimetic.

In certain embodiments, the clathrin-dependent endocytosis inhibitor is a dynamin GTPase inhibitor. In a further embodiment, the dynamin GTPase inhibitor is dynasore. Dynasore has the chemical structure of Formula (I):

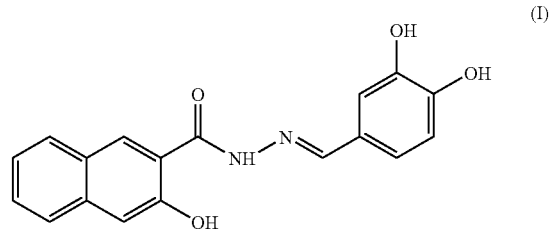 [SMILES: O=C(N/N=C/c1ccc(O)c(O)c1)c1cc2ccccc2cc1O]

The present invention also encompasses a method of treating a condition characterized by decreased TGF-β signaling. Conditions characterized by decreased TGF-β signaling include, but are not limited to inflammatory conditions, autoimmune diseases, cancer, cardiovascular disease and certain skin conditions. Inflammatory conditions include, but are not limited to multiple sclerosis. In certain embodiments, the inflammatory condition is selected from the group consisting of Alzheimer's disease, asthma, chronic obstructive pulmonary disease, multiple sclerosis, rheumatoid arthritis, atherosclerosis, Guillan-Barre syndrome, systemic lupus erythematosus. In another embodiment, the inflammatory condition is atherosclerosis.

In one aspect, the invention is a method of treating a cardiovascular disease in a patient in need thereof comprising administering to the patient a therapeutically effective amount of a clathrin-dependent endocytosis inhibitor.

The invention is also directed to a method of treating a skin condition characterized by abnormal proliferation and/or growth of cutaneous tissue. Exemplary diseases are psoriasis, basal cell carcinoma, squamous cell carcinoma, keratoacanthoma, actinic keratosis, X-linked ichthyosis, acne, dermatitis and epidermolytic hyperkeratosis.

The invention is additionally directed to a method for the treatment of cancer comprising administering a clathrin-dependent endocytosis inhibitor in a therapeutically effective amount. Exemplary cancers include malignant tumors, adenocarcinomas, carcinomas, sarcomas, malignant neoplasms, leukemias and epithelial cell derived cancers. Examples of epithelial cell derived cancers include, but are not limited to, breast cancer, colon cancer, ovarian cancer, lung cancer or prostate cancer. In an additional embodiment, the method relates to the treatment of a condition selected from the group consisting of a melanoma, myeloma and lymphoma comprising administering a clathrin-dependent endocytosis inhibitor. The cancer treated by the inventive method can be of any origin such as chromosomal abnormalities, degenerative growth and developmental disorders, mitogenic agents, ultraviolet radiation (UV), viral infections, oncogenes, mutations in genes, inappropriate expression of a gene and presentation on a cell, or carcinogenic agent.

In another embodiment, the invention is directed to a method of treating a condition characterized by decreased TGF-β signaling comprising administering a clathrin-dependent endocytosis inhibitor in a therapeutically effective amount, wherein the condition characterized by decreased TGF-β signaling is not a condition caused by *Chlamydia pneumoniae* infection.

In other embodiments, the invention is directed to a method of inhibiting carcinogenesis comprising administering a clathrin-dependent endocytosis inhibitor in a therapeutically effective amount. Inhibition of carcinogenesis encompasses preventing the occurrence of the cancer or a precancerous condition or to slow, halt or reverse the progression of the cancer or a precancerous condition. Precancerous conditions include, for example, hyperplasia, metaplasia, dysplasia, oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

In another aspect, the invention is a method of treating a cardiovascular disease in a patient in need thereof comprising administering a clathrin-dependent endocytosis inhibitor in a therapeutically effective amount. In a further aspect, the invention is a method of treating a cardiovascular disease comprising administering dynasore in a therapeutically effective amount. In one embodiment, the cardiovascular disease is atherosclerosis. In additional embodiments, the invention further comprises the administration of a 3-hydroxy-3-methyl-glutaryl coenzyme A (HMG-CoA) reductase inhibitor. In a further embodiment, the HMG-CoA reductase inhibitor is a statin. Exemplary statins include lovastatin, simvastatin, pravastatin, fluvastatin, atorvastatin, itavastatin, rosuvastatin and rivastatin. The invention is also directed to preventing myocardial infarction comprising administering a clathrin-dependent endocytosis inhibitor to a patient at risk of suffering from myocardial infarction. A patient at risk for suffering from myocardial infarction is a patient with an elevated low density lipoprotein (LDL) level, a patient suffering from atherosclerosis.

As used herein, "treating" or "treatment" includes preventing or delaying the onset of the symptoms, complications, or biochemical indicia of a disease, or alleviating or ameliorating the symptoms or arresting or inhibiting further development of the disease, condition, or disorder. A "therapeutically effective amount" is an amount which, alone or in combination with one or more other active agents, can control, decrease, inhibit, ameliorate, prevent or otherwise affect one or more symptoms of a disease or condition to be treated. As used herein, a therapeutically effective amount of a clathrin-dependent endocytosis inhibitor is an amount sufficient to enhance TGF-β signaling.

The invention also encompasses a pharmaceutical composition comprising a therapeutically effective amount of a clathrin-dependent endocytosis inhibitor and a HMG-CoA reductase inhibitor. In one embodiment, the clathrin-dependent endocytosis inhibitor is dynasore. In another embodiment, the HMG-CoA reductase inhibitor is a statin.

The pharmaceutical composition comprises a pharmaceutically acceptable carrier or excipient. The pharmaceutically acceptable carrier or excipient is chosen based on the expected route of administration of the composition in therapeutic applications. The route of administration of the composition depends on the condition to be treated. For example, intravenous injection may be preferred for treatment of a systemic disorder such as a leukemia or lymphoma, and oral administration may be preferred to treat a disease affecting the gastrointestinal system. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the composition can be administered orally, parenterally, intranasally, vaginally, rectally, lingually, sublingually, buccally, intrabuccaly and transdermally to the patient.

Accordingly, compositions designed for oral, lingual, sublingual, buccal and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like.

The compositions of the present invention can be administered parenterally such as, for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampoules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pectin composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

The following Examples further illustrate the present invention but should not be construed as in any way limiting its scope.

EXEMPLIFICATION

Example 1

Enhancement of TGF-β Signaling and Responses by Clathrin-Dependent Endocytosis Inhibitors Abstract Clathrin-dependent endocytosis is believed to be involved in TGF-β-stimulated cellular responses but the subcellular locus where TGF-β induces signaling remains unclear. Here we demonstrate that clathrin-dependent endocytosis inhibitors, which are known to arrest the progression of endocytosis at coated-pit stages, inhibit cell-surface-bound TGF-β internalization and promote co-localization and accumulation of TβR-I and SARA at the plasma membrane. These inhibitors enhance TGF-β-induced signaling and cellular responses (Smad2 phosphorylation/nuclear localization and PAI-1 expression). Dynasore, a newly identified inhibitor of dynamine GTPase activity, is one of the most potent inhibitors among those tested and is a potent TGF-β enhancer as well. Dynasore ameliorates atherosclerosis in the aortic endothelium of hypercholesterolemic ApoE-null mice by counteracting suppressed TGF-β responsiveness caused by the hypercholesterolemia, presumably acting via its effect on TGF-β endocytosis and signaling in vascular cells.

Transforming growth factor (TGF-β) is a family of pleiotrophic cytokines which includes TGF-$\beta_1$, -$\beta_2$ and -$\beta_3$ in mammals. It is a bifunctional growth regulator[1]. It inhibits growth of most cell types including epithelial cells, endothelial cells and lymphocytes but stimulates growth of mesenchymal cells. The growth regulatory activity of TGF-β has been implicated in carcinogenesis, immunomodulation and cellular differentiation. TGF-β is the most potent known stimulator for extracellular matrix synthesis and deposition and plays an important role in wound healing and tissue fibrosis. It has anti-inflammatory and pro-inflammatory activities, depending on the tissue studied. Because of its anti-inflammatory and immunomodulatory activities, TGF-β is a protective cytokine for atherosclerosis in the cardiovascular system[2,3].

TGF-β stimulates cellular responses by inducing formation of a heterooligomeric TGF-β receptor complex at the plasma membrane[4,5]. Within this complex, the constitutively active type II TGF-β receptor (TβR-II) phosphorylates and activates the type I TGF-β receptor (TβR-I). The activated TβR-I phosphorylates Smad2 and Smad3; the phosphorylation is facilitated by the Smad anchor protein called Smad anchor for receptor activation (SARA)[6,7]. Phosphorylated Smad2/Smad3 associates with Smad4 to form heterotrimeric complexes which translocate to and accumulate in the nucleus, where they regulate transcription of responsive genes. Smad7, a negative regulator of TGF-β signaling, is associated with lipid rafts/caveolae and mediates TGF-β/TGF-β receptor degradation[8,9]. The cellular responses to TGF-β are determined by TGF-β partitioning between clathrin-dependent and caveolae-dependent endocytosis pathways[3,8-12]. The former promotes signaling and cellular responses whereas the latter leads to rapid degradation of TGF-β/TGF-β receptors and attenuation of TGF-β responsiveness[8-12]. Although clathrin-dependent endocytosis is involved in signaling[3,6-15], the subcellular locus where TGF-β induces signaling remains unclear[16].

Endosomes are believed to be important mediators of TGF-β-induced signaling[3,8-15]. This is based on the observations that TGF-β receptor internalization and TGF-β-induced cellular responses are inhibited by overexpression of dynamin dominant negative mutant K44A[8] and that SARA colocalizes with endosome markers in endosomes[8,13]. However, Lu et. al[16] demonstrated that overexpression of dynamin K44A inhibited TGF-β-induced TGF-β receptor internalization without altering TGF-β-induced signaling and cellular responses. These conflicting results regarding the role of endocytosis in TGF-β-induced signaling and responses could be due to the different levels of dynamin K44A expression in the experimental systems used[8,16]. To define the subcellular locus of TGF-β-induced signaling, we have determined the effects of several known clathrin-dependent endocytosis inhibitors, including the dynamin inhibitor dynasore[17,18], on TGF-β-induced signaling and cellular responses. This approach is an alternative to studying overexpression of dynamin K44A which could yield variable results depending on the expression level.

A number of compounds have been shown to inhibit clathrin-dependent endocytosis. These include methyl-β-cyclodextrin (β-CD)[19], phenothiazines[20-22], monodansylcadaverine (MDC)[23], chloroquine[24], monensin[25], hyperosmotic sucrose[26] and dynasore[17,18]. β-CD inhibits clathrin-dependent endocytosis by selectively extracting cholesterol from the plasma membrane. Hydrophobic amines such as phenothiazines, MDC and chloroquine inhibit clathrin-dependent endocytosis by affecting the function of clathrin and clathrin-coated vesicles[20,24]. Monensin is a monovalent ionophore which inhibits clathrin-dependent endocytosis by dissipating a proton gradient[25]. Hyperosmotic sucrose inhibits clathrin-dependent endocytosis by preventing clathrin and adaptors from interacting[26]. Dynasore is a cell-permeable inhibitor of dynamin GTPase activity which facilitates the formation of coated pits in the process of endocytosis[17,18].

Figure 1J:
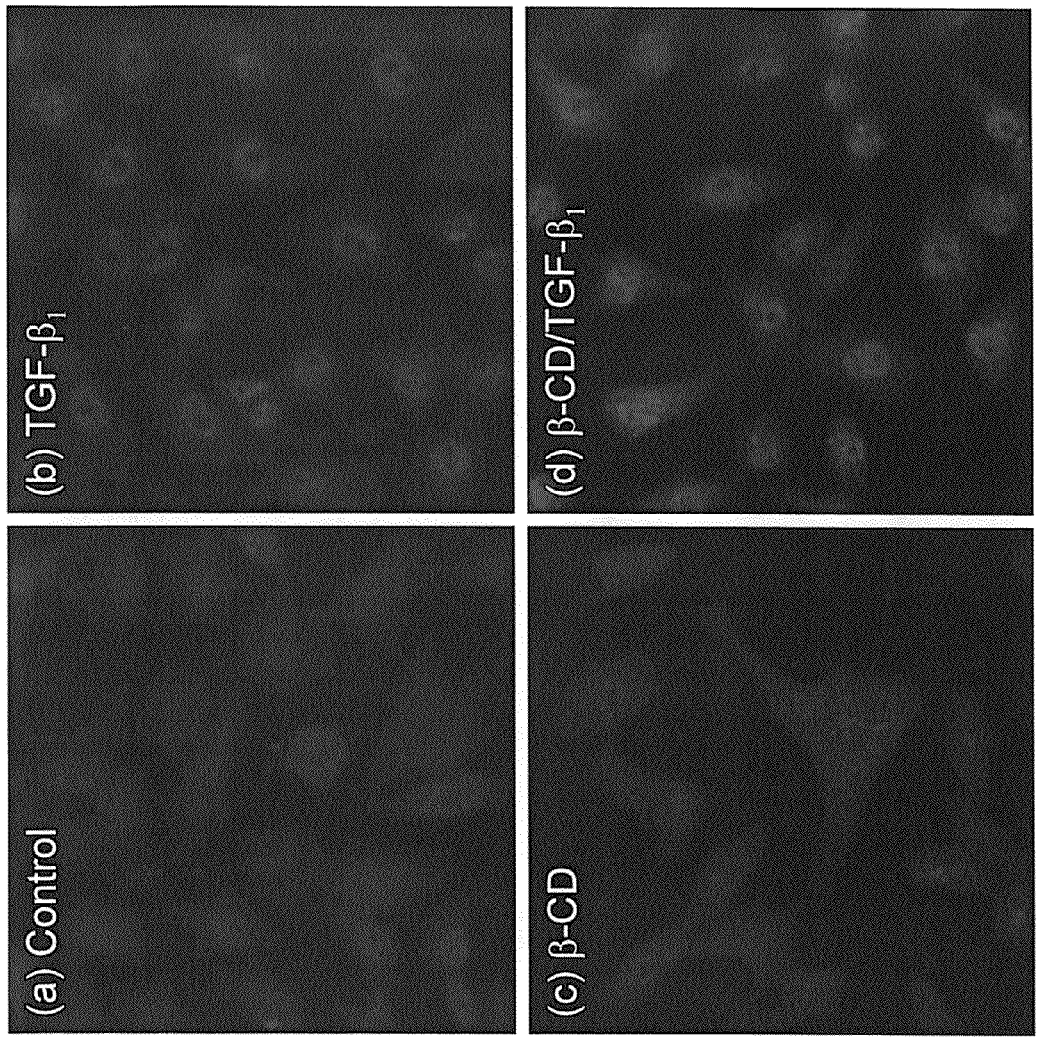

If TGF-β-induced signaling occurs in endosomes, as reported previously[6-15], inhibitors of clathrin-dependent endocytosis would be expected to attenuate TGF-β-stimulated signaling such as Smad2 phosphorylation and nuclear colocalization[4,5]. To test this, Mv1Lu cells were pretreated with vehicle only or with clathrin-dependent endocytosis inhibitors at 37° C. for 30 min and then treated with or without 100 pM TGF-$β_1$. After several time periods, the relative levels of P-Smad2 in treated and stimulated cells were analyzed by quantitative Western blot analysis using antibodies to P-Smad2 and Smad2. As shown in FIG. 1, β-CD, MDC, monensin and triflupromazine (TFP) enhanced TGF-$β_1$-stimulated Smad2 phosphorylation in a time-dependent manner (FIGS. 1Aa, 1Ba, 1Ca and 1Da, respectively). After stimulation of cells with TGF-$β_1$ for 60 min, β-CD, TFP, MDC and monensin enhanced TGF-$β_1$-stimulated Smad2 phosphorylation by ~1.5-2.5 fold (FIGS. 1Ab, 1Bb, 1Cb, and 1Db). To further characterize the effects of these inhibitors on Smad2 phosphorylation, Mv1Lu cells were pretreated with vehicle only or with several concentrations of the inhibitors at 37° C. for 30 min and then stimulated with 100 pM of TGF-$β_1$. After 30 min at 37° C., cell lysates were subjected to Western blot analysis using antibodies to P-Smad2 and Smad2 followed by quantitation with densitometry. As shown in FIG. 1E to 1I, β-CD, TFP, monensin, chloroquine and dynasore enhanced TGF-$β_1$-stimulated Smad2 phosphorylation in a concentration-dependent manner. β-CD at 10 mg/ml, TFP (24 μM), monensin (40 μM), chloroquine (200 μM) and dynasore (40 μM), enhanced TGF-$β_1$-stimulated Smad2 phosphorylation by ~2-3 fold. To determine the effect of β-CD on TGF-$β_1$-stimulated nuclear localization of P-Smad2, Mv1Lu cells were pretreated with vehicle only or with β-CD (10 mg/ml). After 1 h at 37° C., cells were stimulated with TGF-$β_1$ (10 pM) for 30 min. The nuclear localization of P-Smad2 was then analyzed by indirect fluorescent staining. As shown in FIG. 1J, β-CD and TGF-$β_1$ together promoted nuclear localization of P-Smad2 (d) whereas each alone did not promote it (b and c).

Figure 1K:
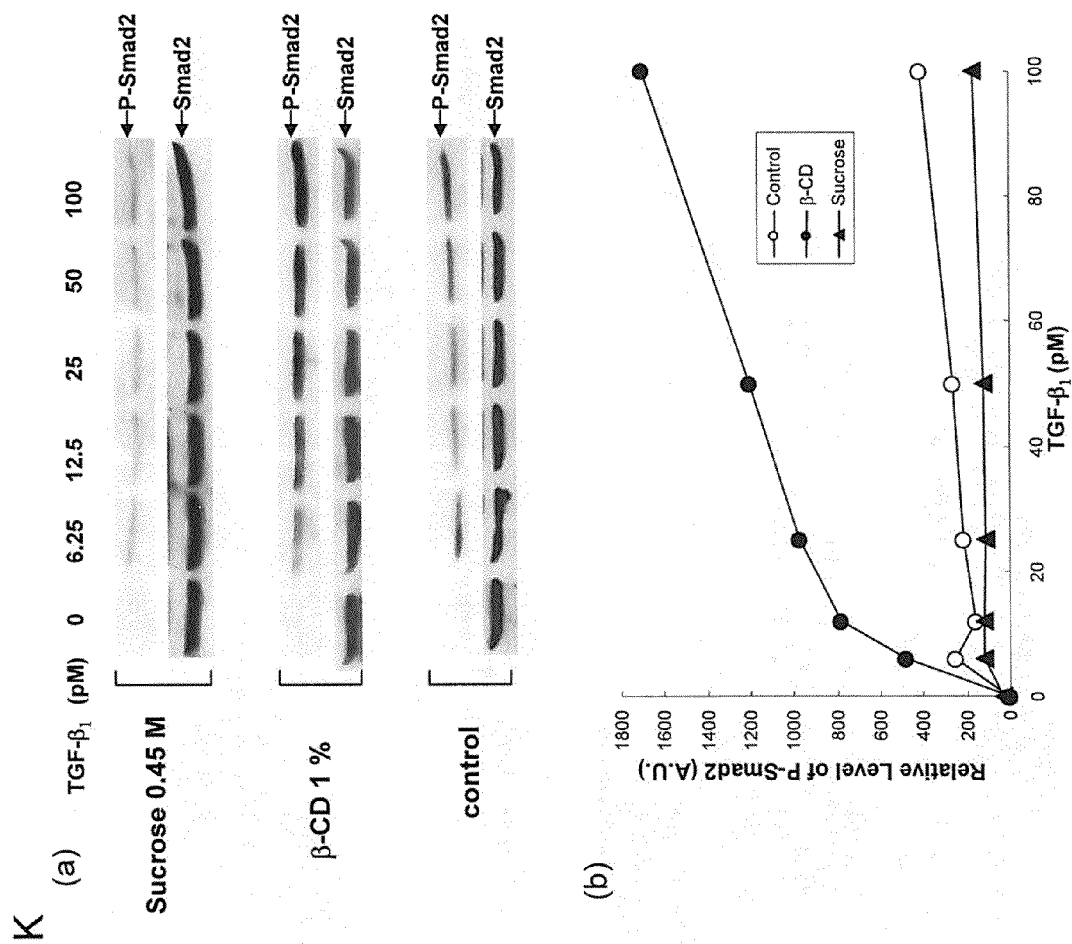

The endocytosis inhibitors tested here have been shown to inhibit the pinching-off of endocytic vesicles from the plasma membrane (formation of endosomes) and arrest the endocytosis process at coated-pit stages[17-26]. This suggests that the coated-pit stages in the process of clathrin-dependent endocytosis may play important roles in mediating TGF-β-induced signaling. To define the coated-pit stages that are important in TGF-$β_1$-induced signaling, we treated Mv1Lu cells with hyperosmotic sucrose (0.45 M) or β-CD and examined TGF-$β_1$-stimulated Smad2 phosphorylation in these cells. Hyperosmotic sucrose is known to inhibit the formation of shallow coated pits (type 1 coated pits) or receptor clustering[26]. β-CD has been shown to inhibit progression from shallow coated pits (type 1 coated pits) to invaginated coated pits (type 2 coated pits) in the clathrin-dependent endocytosis process[19]. As shown in FIG. 1K, hyperosmotic sucrose inhibited TGF-$β_1$-stimulated Smad2 phosphorylation in the cells treated with various concentrations of TGF-$β_1$ (FIGS. 1Ka and 1Kb). In cells stimulated with 100 pM TGF-$β_1$, hyperosmotic sucrose attenuated Smad2 phosphorylation by ~60% (FIG. 1Kb). On the other hand, β-CD enhanced TGF-$β_1$-stimulated Smad2 phosphorylation at all concentrations of TGF-$β_1$. It enhanced TGF-$β_1$-stimulated Smad2 phosphorylation by 2-4 fold when compared with the control (treatment without β-CD) (FIGS. 1Ka and 1Kb). These results suggest that TGF-β-induced signaling occurs at the type 1 coated-pit stage.

Figure 2:
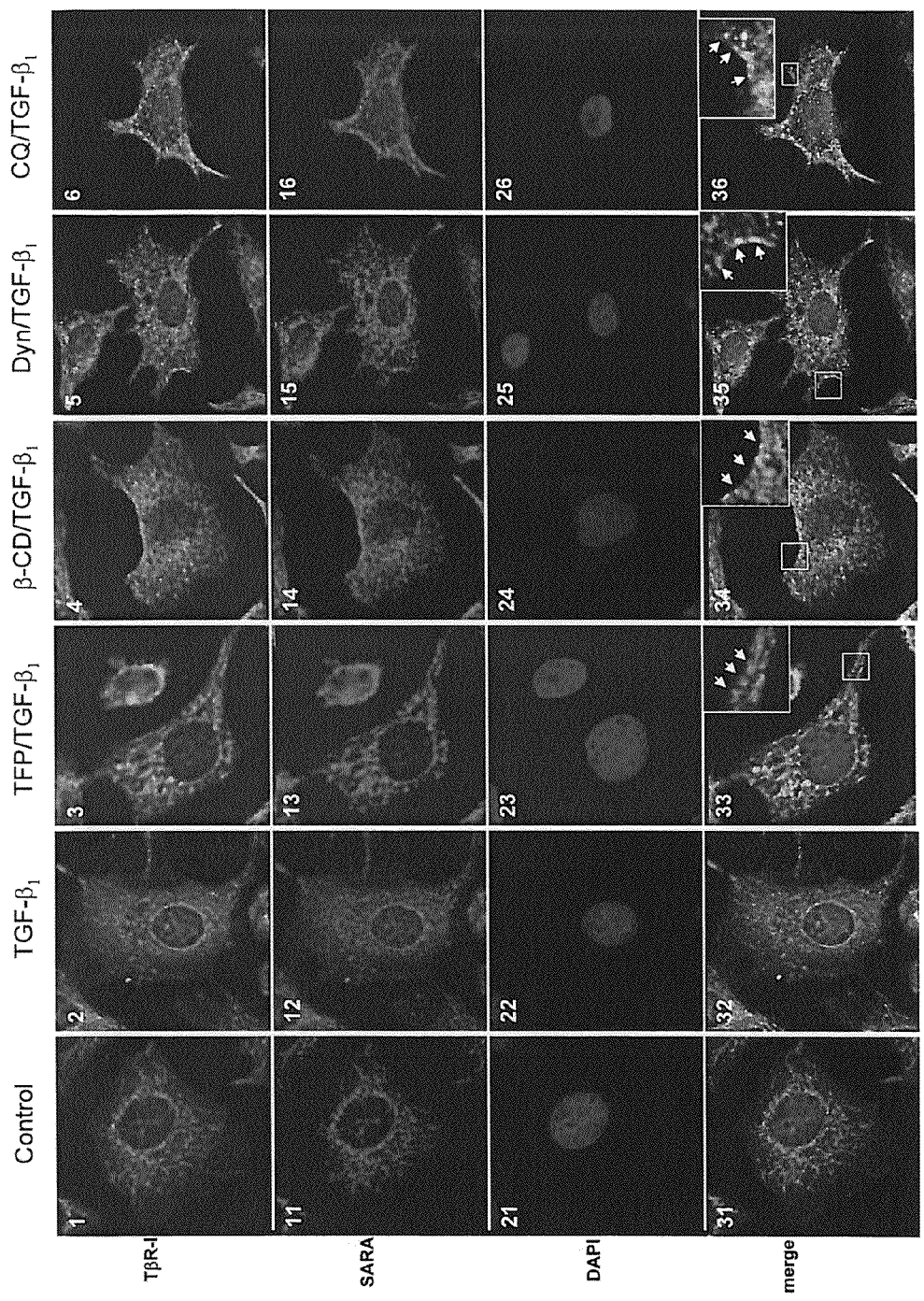
FIG. 2 shows enhancement of accumulation and co-localization of SARA and TβR-I at the plasma membrane by clathrin-dependent endocytosis inhibitors in Mv1Lu cells. Cells were pretreated with vehicle only or 20 μM TFP, 10 mg/ml β-CD, 40 μM dynasore (Dyn) and 200 μM chloroquine (CQ) at 37° C. for 1 h. Treated cells were then stimulated with and without 100 pM TGF-$β_1$. After 30 min at 37° C., cells were fixed and analyzed by indirect immunofluorescent staining using antibody to TβR-I (panels 1-10) and SARA (panels 11-20), DAPI (nuclear) staining was also performed (panels 21-30). Merged staining is also shown (panels 31-40). Insets indicate the co-localization and accumulation of SARA and TβR-I at the plasma membrane.
Figure 2:
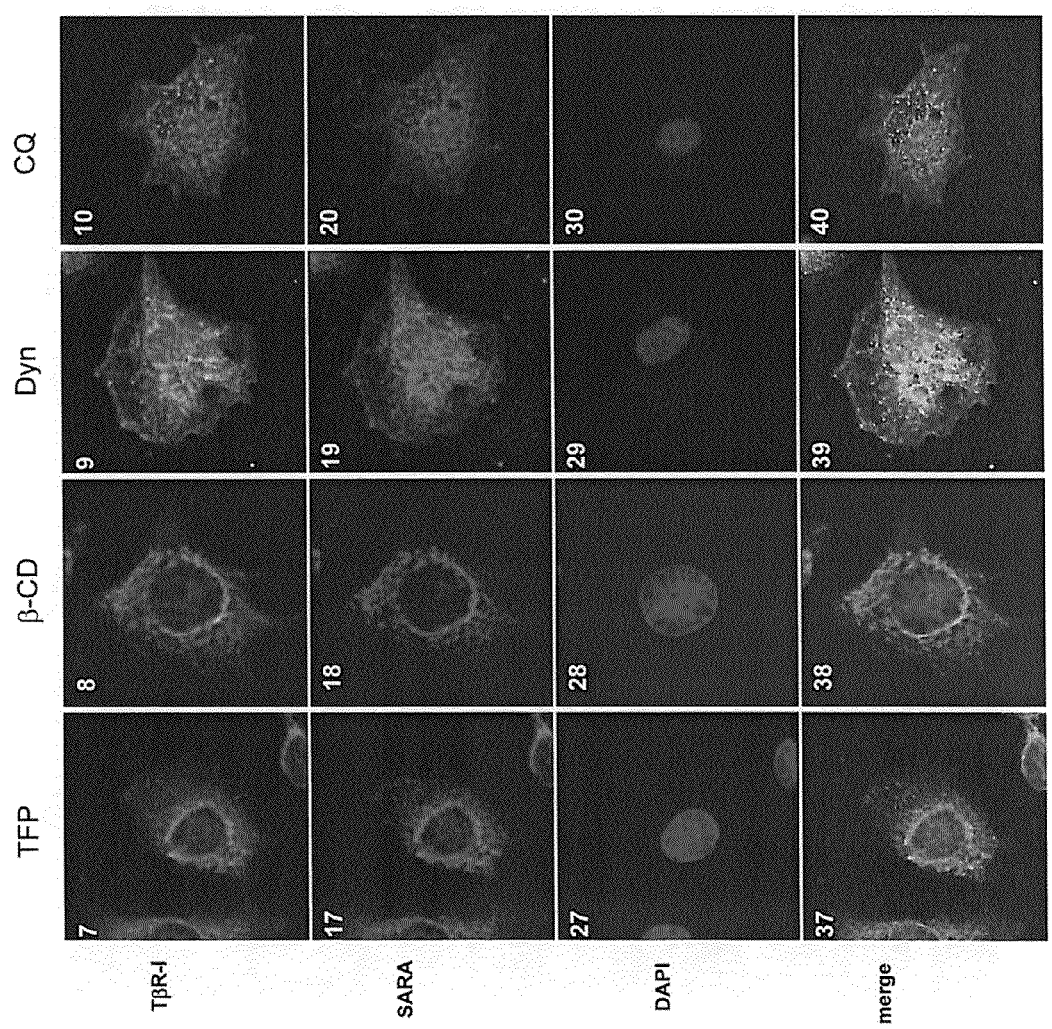

TGF-β stimulates Smad2 phosphorylation by inducing association of TβR-I and SARA[6,7] (which serves as an anchor for Smad2), binding of Smad2 to SARA, and subsequent phosphorylation of Smad2 by TβR-I in the TβR-1-SARA-Smad2 complex. If clathrin-dependent endocytosis inhibitors enhance TGF-β-induced signaling (TGF-β-stimulated Smad2 phosphorylation) by increasing accumulation of TβR-I/TβR-II complexes at the coated pits, they should promote co-localization and accumulation of TβR-I and SARA at the plasma membrane. To test this, Mv1Lu cells were stimulated with 100 pM TGF-$β_1$. After 30 min at 37° C., cells were treated with the inhibitors and analyzed by immunofluorescent microscopy using antibodies to TβR-I and SARA. As shown in FIG. 2, TGF-$β_1$ alone stimulated co-localization and accumulation of TβR-I and SARA in endocytic vehicles (endosomes) (FIG. 2, panel 32 versus panel 31) in Mv1Lu cells. This is consistent with the previous report that TGF-β enhances TGF-β receptor internalization[16]. However, co-treatment of cells with TGF-$β_1$ and TFP, β-CD, dynasore or chloroquine promoted co-localization and accumulation of TβR-I and SARA at the plasma membrane in these cells (FIG. 2, panels 33-36, inset). These endocytosis inhibitors alone did not cause co-localization and accumulation of TβR-I and SARA at the plasma membrane (FIG. 2, panels 37-40 versus panel 31). These results support the notion that clathrin-dependent endocytosis inhibitors enhance TGF-β-induced signaling (or TGF-β-stimulated Smad2 phosphorylation and nuclear localization) by promoting localization and accumulation of SARA-TGF-β receptor complexes at the plasma membrane or coated-pit stages.

Figure 3B:
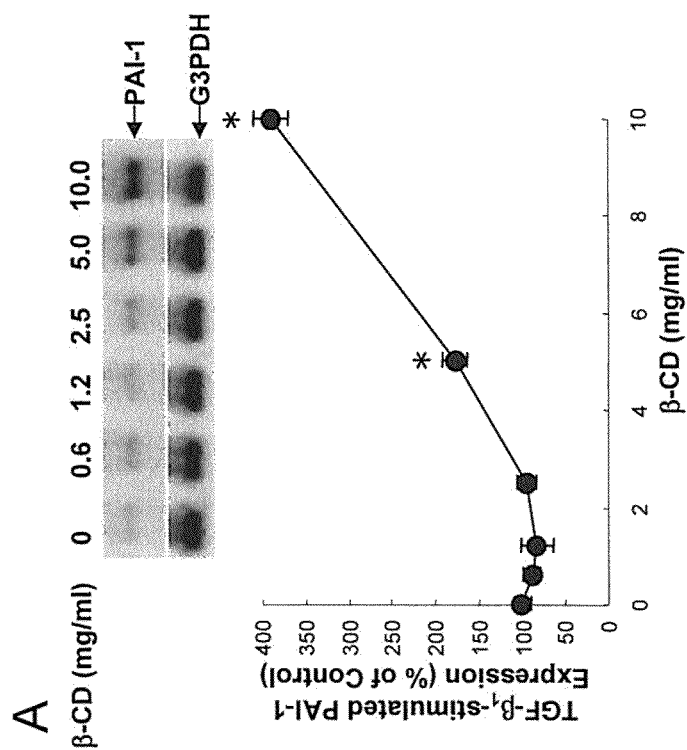
FIG. 3 shows enhancement of TGF-β-stimulated expression of PAI-1 by clathrin-dependent endocytosis inhibitors in Mv1Lu cells. (A-G) Cells were pretreated with vehicle only or with several concentrations (as indicated) of β-CD (A,C), thioridazine (B), TFP (D), chloroquine (E), monensin (F) and MDC (G) at 37° C. for 1 h. Treated cells were then stimulated with 50 pM TGF-$β_1$. After 2 h at 37° C., the mRNAs of PAI-1 and G3PDH (as control) in the cell lysates were analyzed by Northern blot (top) and quantified using a PhosphoImager (bottom) (A,B) or real-time RT-PCR (C to G). The TGF-β-stimulated expression of PAI-1 in cells treated with vehicle only was taken as 100% (A, B) or 1 fold (C to G) of control. Experiments were carried out in triplicate. *Significantly higher than control treated without the inhibitor, p<0.001. **Significantly higher than control, p<0.05. (H) Cells were pretreated with several concentrations (as indicated) of dynasore at 37° C. for 1 h and then stimulated with 50 pM TGF-$β_1$. After 2 h at 37° C., the mRNA of PAI-1 was quantitated by real-time RT-PCR. The relative level of PAI-1 mRNA in cells treated with TGF-$β_1$ alone was taken as 1 (100%). Experiments were carried out in triplicate. The data shown is representative of 3 independent experiments.
Figure 3A:
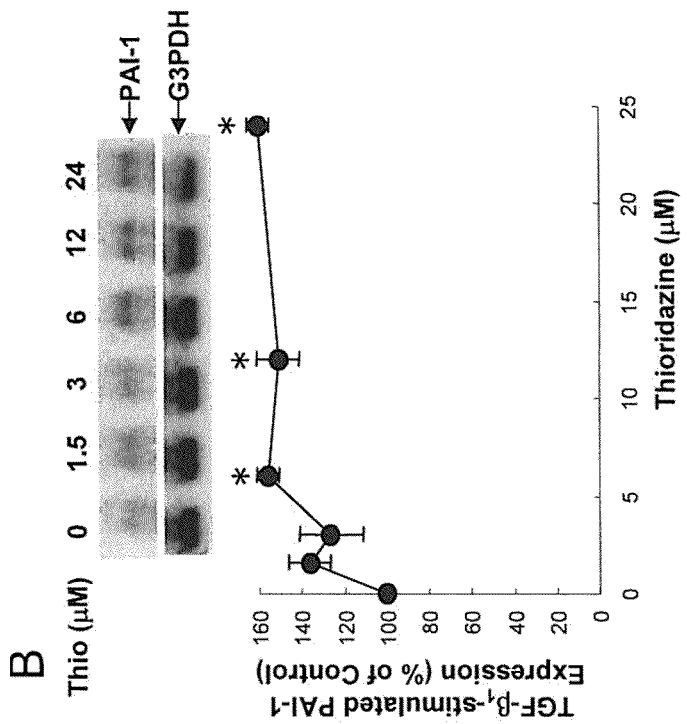
Figures 3C, 3D, 3E, 3F:
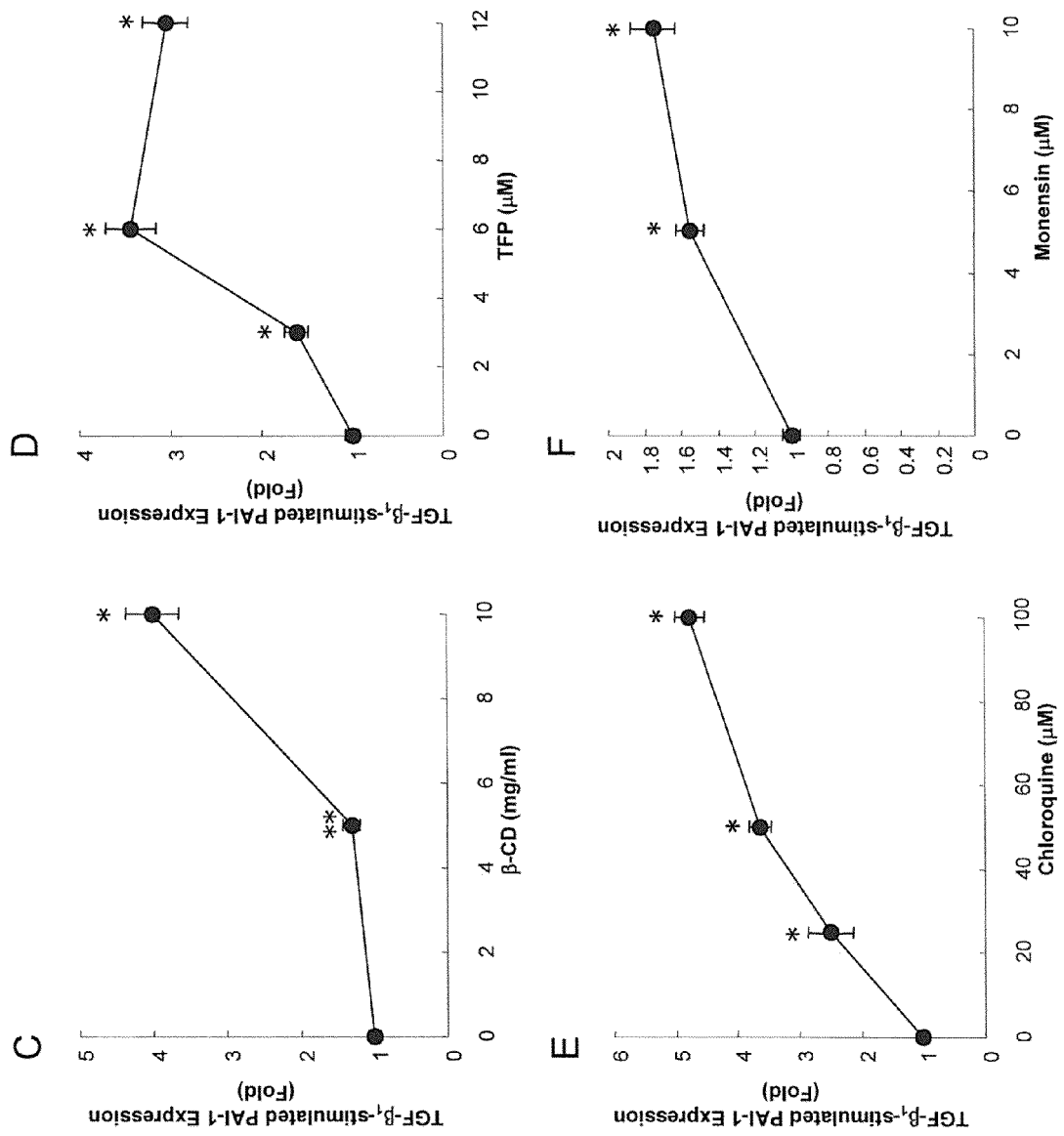
Figures 3G, 3H:
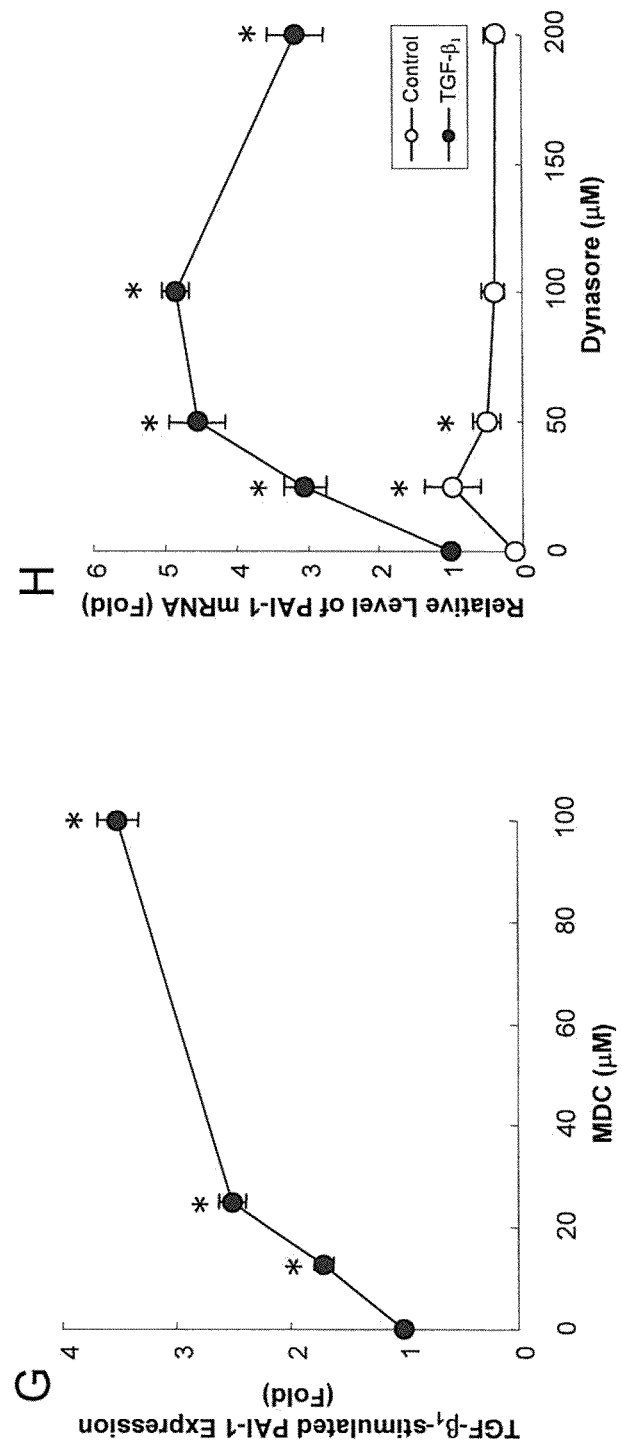

The PAI-1 gene is one of the most studied genes responsive to TGF-β stimulation[4,5]. The promotor region of the PAI-gene contains several Smad2/3 binding sites that have been used as the TGF-β responsive elements to enhance the expression of a reported gene[4,5]. Since clathrin-dependent endocytosis inhibitors are enhancers for TGF-$β_1$-induced signaling, we determined the effects of these inhibitors on TGF-$β_1$-stimulated expression of PAI-1 in Mv1Lu cells. Cells were pretreated with vehicle only and several concentrations of β-CD, thioridazine, TFP, MDC, monensin and chloroquine at 37° C. for 1 h. Cells were then stimulated with 50 pM TGF-$β_1$. After 2 h at 37° C., the relative levels of PAI-1 mRNA were analyzed by quantitative Northern blot analysis (FIGS. 3A and 3B) and real-time RT-PCR (FIG. 3C-3G). As shown in FIG. 3, these inhibitors enhanced TGF-$β_1$-stimulated expression in a concentration-dependent manner. β-CD at 10 mg/ml (A,C), 5 μM thioridazine (B), 6 μM TFP (D), 100 μM chloroquine (E), 10 μM monensin (F) and 100 μM MDC (G) enhanced TGF-$β_1$-stimulated expression of PAI-1 by ~1.8 to 4.5 fold. Since dynasore alone was found to stimulate PAI-1 expression, we determined the effects of several concentrations of dynasore with and without 50 pM TGF-$β_1$ on PAI-1 expression in Mv1Lu cells. As shown in FIG. 3H, dynasore (25 μM) alone stimulated PAI-1 expression to the same extent as with 50 pM TGF-$β_1$ alone. At 50 μM, dynasore enhanced TGF-$β_1$-stimulated PAI-1 expression by ~5 fold.

Figure 4A:
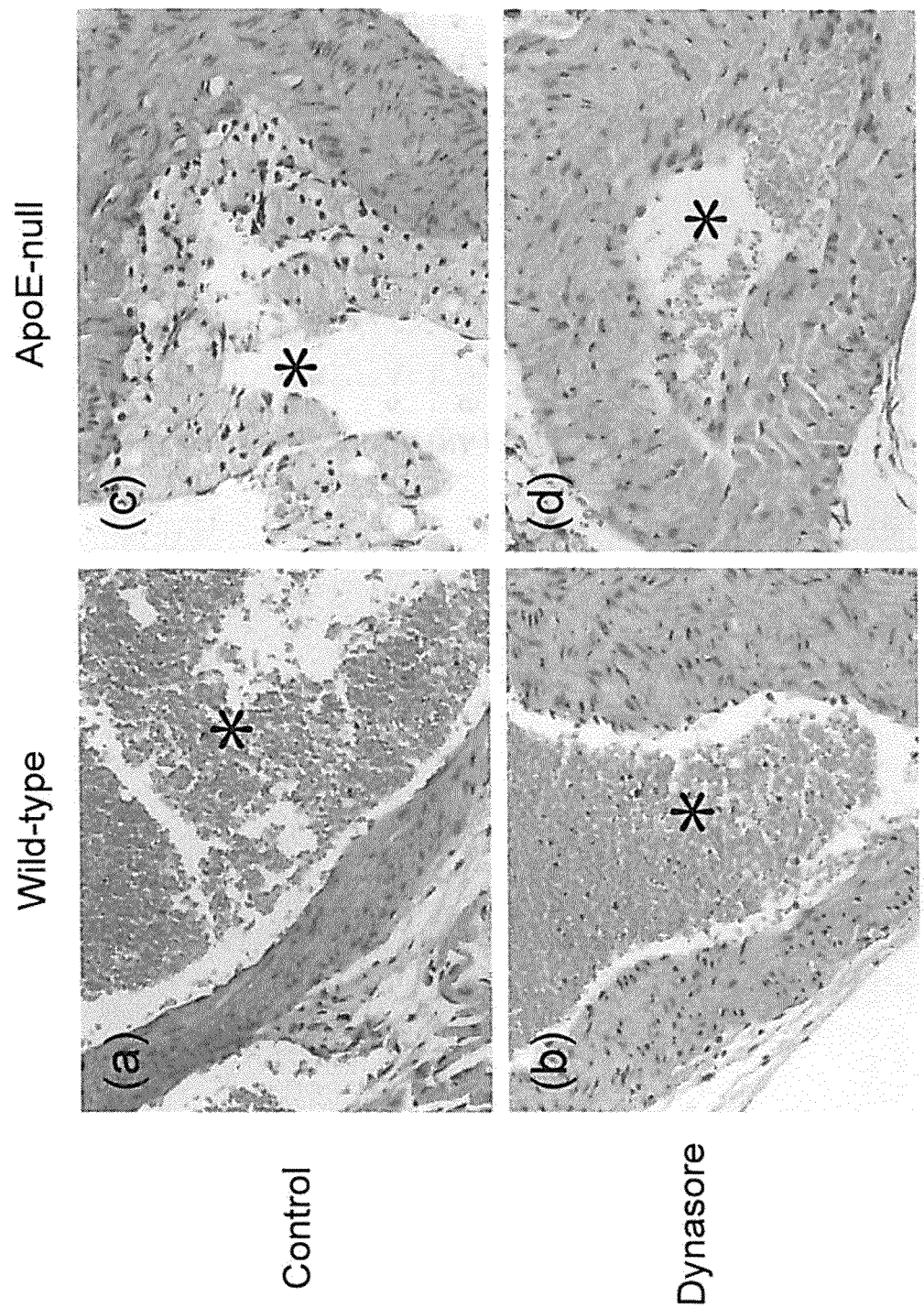
FIG. 4 shows Histological analysis (A) and TβR-II immunofluorescent staining (B) of the coronary arteries of wild-type and ApoE-null mice. Wild-type and ApoE-null mice were treated with vehicle only (a, c) or 1 mg/kg dynasore (b, d) every two days for 8 weeks. The coronary arteries were removed from the animals and subjected to histological analysis by H & E staining (A) and indirect immunofluorescent staining for TβR-II(B). The asterisk (*) indicates the location of the lumen in coronary arteries. The arrow indicates the immunofluorescent staining of TβR-II in the aortic endothelium.

Suppressed TGF-β responsiveness in vascular cells has recently been found to play an important role in the pathogenesis of atherosclerosis induced by hypercholesterolemia[3,12]. We hypothesize that TGF-β enhancers such as inhibitors of clathrin-dependent endocytosis may ameliorate atherosclerosis caused by cholesterol-induced suppression of TGF-β responsiveness in vascular cells[3,12]. To test our hypothesis, we treated hypercholesterolemic ApoE-null mice with dynasore (1 mg/kg body weight) via intraperitoneal administration every two days for 8 weeks. We chose dynasore for two reasons. These include: 1) Among inhibitors we tested, dynasore is one of the most potent TGF-β enhancers in Mv1Lu cells and other cell types including bovine aortic endothelial cells (BAEC cells) and Chinese hamster ovary cells (CHO cells) (unpublished results). At 50 μM, it enhances TGF-β-stimulated expression of PAI-1 in these cell types by ~4-5 fold, 2) Dynasore is the only inhibitor tested which alone is capable of stimulating PAI-1 expression. It is a TGF-β-enhancer as well as a TGF-β mimetic and 3) no apparent macroscopic or microscopic abnormality has been detected in the liver, heart, lung and kidney of wild-type mice following intraperitoneal administration of dynasore (1 mg/kg body weight) every 2 days for 8 weeks. As shown in FIG. 4A, many macrophages or foam cells were attached to the endothelium of coronary arteries in ApoE-null mice (FIG. 4Ac). In contrast, very few macrophages or foam cells were found in the endothelium of the coronary arteries in hypercholesterolemic ApoE-null type mice treated with dynasore (FIG. 4Ad). Dynasore did not affect the plasma levels of cholesterol in ApoE-null mice (460±50 mg/dl in ApoE-null mice treated with dynasore versus 470±61 mg/dl in ApoE-null mice treated without dynasore). In wild-type mice treated with either vehicle only or dynasore, the coronary arteries exhibited normal morphology (FIGS. 4Aa and 4Ab). The plasma levels of cholesterol in wild-type mice treated with either vehicle only or dynasore were 120±10 and 125±20 mg/dl, respectively.

Figure 4B:
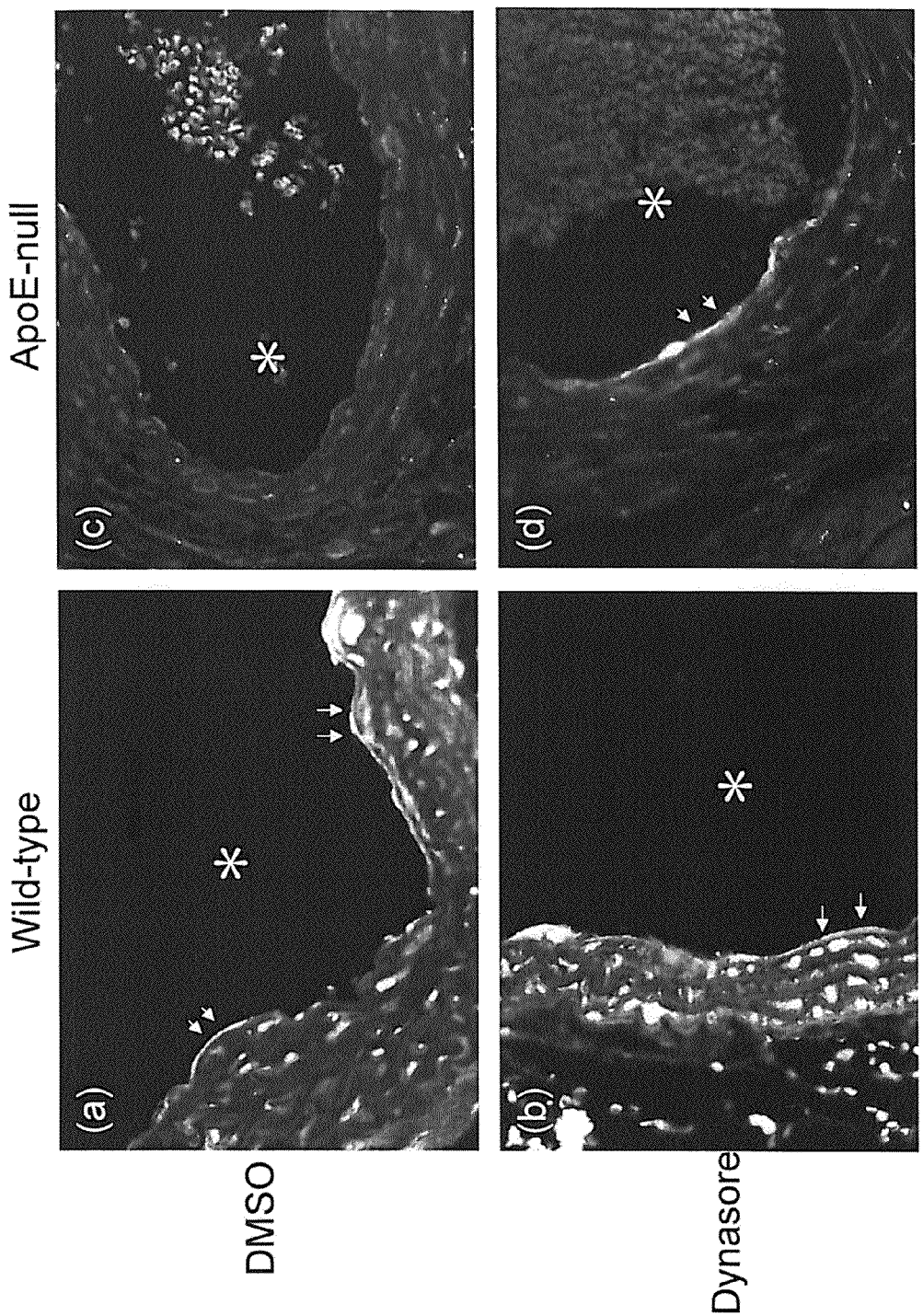

Since hypercholesterolemia has been shown to down-regulate the expression of TβR-II in the aortic endothelium of ApoE-null mice[12], we examined the expression of TβR-II in the animals treated with dynasore. As shown in FIG. 4B, the TβR-II staining was found in the aortic endothelium as well as in the smooth muscle of coronary arteries in wild-type mice treated with either vehicle only or dynasore (FIGS. 4Ba and 4Bb). However, no TβR-II staining was found in the aortic endothelium and smooth muscle of coronary arteries in ApoE-null mice treated with vehicle only (FIG. 4Bc). Dynasore treatment appeared to restore the TβR-II staining in the aortic endothelium of coronary arteries in the animals (FIG. 4Bd). Interestingly, slight staining of TβR-II was found in the smooth muscle near the endothelium (FIG. 4Bd). These results suggest that dynasore is effective in ameliorating atherosclerosis, at least in part, by counteracting the down-regulation of TβR-II expression caused by hypercholesterolemia in the aortic endothelium of ApoE-null mice[12].

Clathrin-dependent endocytosis inhibitors are known to inhibit the endocytosis process at different steps. Hyperosmotic sucrose blocks formation of type 1 coated pits[19,28]. β-CD and dynasore inhibit progression from type 1 coated pits to type 2 coated pits[17,18]. Phenothiazines, MDC and chloroquine inhibit the progression from type 2 coated pits to type 3 coated pits[23,24]. Monensin and dynasore inhibit progression from type 3 coated pits to coated vesicles[18,25]. All of the inhibitors tested except hyperosmotic sucrose are found to enhance TGF-β-induced signaling and responses. Since these inhibitors arrest endocytosis at coated-pit stages, this suggests that TGF-β-induced signaling mainly occurs at coated-pit stages. This suggestion is supported by the observation that hyperosmotic sucrose inhibits the formation of type 1 coated pits and attenuates TGF-β-induced signaling and responses. Since dynamin is required for both processes leading to formation of type 2 coated pits and coated vesicles, specific inhibition of dynamin by dynasore was expected to block clathrin-dependent endocytosis at these two steps and increase accumulation of coated pits. This would explain why dynasore is a more potent inhibitor for clathrin-dependent cytosis and a more potent TGF-β enhancer than other inhibitors, such as phenothiazines, MDC, and monensin, all of which have been shown to inhibit endocytosis at a single step.

All of these clathrin-dependent endocytosis inhibitors inhibit internalization of cell-surface-bound TGF-β (Supplementary FIG. 1). All inhibitors except hyperosmotic sucrose enhance colocalization and accumulation of TβR-I and SARA at the plasma membrane as demonstrated by immunofluorescence microscopy. This is consistent with their reported activity in arresting the process of endocytosis at the type 1, type 2 or type 3 coated-pit stage[17-26]. It has been demonstrated that overexpression of dynamin K44A enhances accumulation of TβR-I at the plasma membrane[16]. Lu et al[16] reported that overexpression of dynamin K44A inhibits internalization of cell-surface TβR-I but does not affect TGF-β-stimulated cellular responses. In fact, their data shows that overexpression of dynamin K44A enhances TGF-β-stimulated responses by ~2 fold when compared to controls in their experimental system. We suggest that overexpression of wild-type dynamin is not an appropriate control for overexpression of K44A cells in their data[16]. Overexpression of wild-type dynamin may enhance TGF-β-stimulated cellular responses (expression of 3TP-luciferase and ARE-luciferase) by promoting endocytosis and thus increasing formation of coated pits[16]. On the other hand, overexpression of K44A dynamin may enhance TGF-β-stimulated cellular responses by arresting endocytosis at the coated-pit stages[16].

We recently found that cholesterol suppresses TGF-β responsiveness in cultured cells and in the aortic endothelium of ApoE-null mice with hypercholesterolemia[3,12]. Since accumulating evidence indicates that TGF-β in blood is a protective cytokine for atherosclerosis (3-7), this suggests that hypercholesterolemia causes atherosclerosis, at least in part, by suppressing TGF-β responsiveness[3,12]. Here we demonstrate that dynasore, a potent TGF-β enhancer, effectively ameliorates atherosclerosis in ApoE-null mice, presumably by counteracting suppressed TGF-β responsiveness caused by hypercholesterolemia[3,12]. Since the down-regulation of TGF-β levels and/or TGF-β responsiveness has been implicated in other disease processes, such as autoimmune disease[29], potent TGF-β-enhancers such as dynasore or dynasore-like compounds are potential therapeutic compounds for treating such diseases.

References
1. Roberts, A. B. Molecular and cell biology of TGF-beta. Miner. Electrolyte *Metab.* 24, 111-9 (1998).
2. Metcalfe, J. C. & Grainger, D. J. Transforming growth factor-beta and the protection from cardiovascular injury hypothesis. *Biochem. Soc. Trans.* 23, 403-6 (1995).
3. Chen, C. L. et al. Cholesterol suppresses cellular TGF-beta responsiveness: implications in atherogenesis. *J. Cell Sci.* 120, 3509-21 (2007).
4. Heldin, C. H., Miyazono, K. & ten Dijke, P. TGF-beta signalling from cell membrane to nucleus through SMAD proteins. *Nature* 390, 465-71 (1997).
5. Massague, J. TGF-beta signal transduction. *Annu. Rev. Biochem.* 67, 753-91 (1998).
6. Tsukazaki, T., Chiang, T. A., Davison, A. F., Attisano, L. & Wrana, J. L. SARA, a FYVE domain protein that recruits Smad2 to the TGFbeta receptor. *Cell* 95, 779-91 (1998).

7. Xu, L., Chen, Y. G. & Massague, J. The nuclear import function of Smad2 is masked by SARA and unmasked by TGFbeta-dependent phosphorylation. *Nature Cell Biology* 2, 559-62 (2000).
8. Di Guglielmo, G. M., Le Roy, C., Goodfellow, A. F. & Wrana, J. L. Distinct endocytic pathways regulate TGF-beta receptor signalling and turnover. *Nat. Cell Biol.* 5, 410-21 (2003).
9. Ito, T., Williams, J. D., Fraser, D. J. & Phillips, A. O. Hyaluronan regulates transforming growth factor-beta1 receptor compartmentalization. *J. Biol. Chem.* 279, 25326-32 (2004).
10. Le Roy, C. & Wrana, J. L. Clathrin- and non-clathrin-mediated endocytic regulation of cell signalling. *Nat. Rev. Mol. Cell Biol.* 6, 112-26 (2005).
11. Chen, C.-L., Huang, S. S. & Huang, J. S. Cellular heparan sulfate negatively modulates transforming growth factor-beta responsiveness in epithelial cells. *J. Biol. Chem.* 281, 11506-11514 (2006).
12. Chen, C. L., Huang, S. S. & Huang, J. S. Cholesterol modulates cellular TGF-beta responsiveness by altering TGF-beta binding to TGF-beta receptors. *J. Cell. Physiol.* 215, 223-233 (2008).
13. Hayes, S., Chawla, A. & Corvera, S. TGF beta receptor internalization into EEA1-enriched early endosomes: role in signaling to Smad2. *J. Cell Biol.* 158, 1239-49 (2002).
14. Penheiter, S. G. et al. Internalization-dependent and -independent requirements for transforming growth factor beta receptor signaling via the Smad pathway. *Mol. Cell. Biol.* 22, 4750-9 (2002).
15. Mitchell, H., Choudhury, A., Pagano, R. E. & Leof, E. B. Ligand-dependent and -independent transforming growth factor-beta receptor recycling regulated by clathrin-mediated endocytosis and Rab11. *Mol. Biol. Cell* 15, 4166-78 (2004).
16. Lu, Z. et al. Transforming growth factor beta activates Smad2 in the absence of receptor endocytosis. *J. Biol. Chem.* 277, 29363-8 (2002).
17. Macia, E. et al. Dynasore, a cell-permeable inhibitor of dynamin. *Dev. Cell* 10, 839-50 (2006).
18. Nankoe, S. R. & Sever, S. Dynasore puts a new spin on dynamin: a surprising dual role during vesicle formation. *Trends Cell Biol.* 16, 607-9 (2006).
19. Rodal, S. K. et al. Extraction of cholesterol with methyl-beta-cyclodextrin perturbs formation of clathrin-coated endocytic vesicles. *Mol. Biol. Cell* 10, 961-74 (1999).
20. Salisbury, J. L., Condeelis, J. S. & Satir, P. Role of coated vesicles, microfilaments, and calmodulin in receptor-mediated endocytosis by cultured B lymphoblastoid cells. *J. Cell Biol.* 87, 132-41 (1980).
21. Horwitz, S. B. et al. Trifluoperazine inhibits phagocytosis in a macrophagelike cultured cell line. *J. Cell Biol.* 91, 798-802 (1981).
22. Kuratomi, Y. et al. Thioridazine enhances lysosomal accumulation of epidermal growth factor and toxicity of conjugates of epidermal growth factor with *Pseudomonas* exotoxin. *Exp. Cell Res.* 162, 436-48 (1986).
23. Schlegel, R., Dickson, R. B., Willingham, M. C. & Pastan, I. H. Amantadine and dansylcadaverine inhibit vesicular stomatitis virus uptake and receptor-mediated endocytosis of alpha 2-macroglobulin. *Proc. Natl. Acad. Sci. U.S.A.* 79, 2291-5 (1982).
24. Wang, L. H., Rothberg, K. G. & Anderson, R. G. Misassembly of clathrin lattices on endosomes reveals a regulatory switch for coated pit formation. *J. Cell Biol.* 123, 1107-17 (1993).
25. Dickson, R. B., Willingham, M. C. & Pastan, I. H. Receptor-mediated endocytosis of alpha 2-macroglobulin inhibition by ionophores and stimulation by Na+ and HCO3(−). *Ann. N.Y. Acad. Sci.* 401, 38-49 (1982).
26. Hansen, S. H., Sandvig, K. & van Deurs, B. Clathrin and HA2 adaptors: effects of potassium depletion, hypertonic medium, and cytosol acidification. *J. Cell Biol.* 121, 61-72 (1993).
27. Zwaagstra, J. C., El-Alfy, M. & O'Connor-McCourt, M. D. Transforming growth factor (TGF)-beta 1 internalization: modulation by ligand interaction with TGF-beta receptors types I and II and a mechanism that is distinct from clathrin-mediated endocytosis. *J. Biol. Chem.* 276, 27237-45 (2001).
28. Mousavi, S. A., Malerod, L., Berg, T. & Kjeken, R. Clathrin-dependent endocytosis. *Biochem. J.* 377, 1-16 (2004).
29. Li, M. O. & Flavell, R. A. Contextual regulation of inflammation: a duet by transforming growth factor-beta and interleukin-10. *Immunity* 28, 468-76 (2008).

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of accelerating wound healing in a patient in need thereof comprising administering to the patient a therapeutically effective amount of a clathrin-dependent endocytosis inhibitor, wherein the clathrin-dependent endocytosis inhibitor is dynasore.

2. A method of treating cardiovascular disease in a patient in need thereof comprising administering to said patient a clathrin-dependent endocytosis inhibitor in a therapeutically effective amount, wherein the clathrin-dependent endocytosis inhibitor is dynasore.

3. A method of treating atherosclerosis in a patient in need thereof comprising administering to said patient a therapeutically effective amount of dynasore.

4. The method of claim 3, further comprising administration of a therapeutically effective amount of a statin.

5. The method of claim 4, wherein the statin is selected from the group consisting of lovastatin, simvastatin, pravastatin, fluvastatin, atorvastatin, itavastatin, rosuvastatin and rivastatin.

6. A method of treating a skin condition characterized by decreased TGF-beta signaling selected from the group consisting of psoriasis, basal cell carcinoma, squamous cell carcinoma, keratoacanthoma, actinic keratosis, C-linked ichthyosis, acne, dermatitis and epidermolytic hyperkeratosis in a patient in need thereof comprising administering to said patient a therapeutically effective amount of dynasore.

7. A pharmaceutical composition comprising a therapeutically effective amount of dynasore, a therapeutically effective amount of a statin and a pharmaceutically acceptable carrier.

8. The composition of claim 7, wherein the statin is selected from the group consisting of lovastatin, simvastatin, pravastatin, fluvastatin, atorvastatin, itavastatin, rosuvastatin and rivastatin.

* * * * *